United States Patent
Shindo

(10) Patent No.: US 8,858,915 B2
(45) Date of Patent: Oct. 14, 2014

(54) THERAPEUTIC OR PROPHYLACTIC AGENT, DETECTION METHOD AND DETECTION AGENT FOR METABOLIC SYNDROME, AND METHOD FOR SCREENING OF CANDIDATE COMPOUND FOR THERAPEUTIC AGENT FOR METABOLIC SYNDROME

(75) Inventor: Takayuki Shindo, Matsumoto (JP)

(73) Assignee: Japan Science & Technology Agency, Saitama (JP)

( * ) Notice: Subject to any disclaimer, the term of this patent is extended or adjusted under 35 U.S.C. 154(b) by 0 days.

(21) Appl. No.: 12/734,864

(22) PCT Filed: Nov. 21, 2008

(86) PCT No.: PCT/JP2008/071212
§ 371 (c)(1),
(2), (4) Date: May 26, 2010

(87) PCT Pub. No.: WO2009/069546
PCT Pub. Date: Jun. 4, 2009

(65) Prior Publication Data
US 2011/0027187 A1    Feb. 3, 2011

(30) Foreign Application Priority Data

Nov. 26, 2007   (JP) ................. 2007-305122

(51) Int. Cl.
| | |
|---|---|
| A61K 49/00 | (2006.01) |
| C07K 14/705 | (2006.01) |
| A01K 67/027 | (2006.01) |
| C12N 15/85 | (2006.01) |
| G01N 33/68 | (2006.01) |
| A61K 38/00 | (2006.01) |
| A61K 48/00 | (2006.01) |
| C12Q 1/68 | (2006.01) |

(52) U.S. Cl.
CPC .......... *G01N 33/6872* (2013.01); *C07K 14/705* (2013.01); *A61K 38/00* (2013.01); *A01K 67/0276* (2013.01); *A01K 2267/0375* (2013.01); *G01N 2800/04* (2013.01); *C12N 15/8509* (2013.01); *A01K 2217/077* (2013.01); *G01N 2500/00* (2013.01); *A01K 2217/206* (2013.01); *A01K 2217/15* (2013.01); *A61K 48/00* (2013.01); *A01K 2267/035* (2013.01); *C12Q 1/6883* (2013.01); *A01K 2227/0105* (2013.01)
USPC .......................................... 424/9.2; 435/6.18

(58) Field of Classification Search
None
See application file for complete search history.

(56) References Cited

U.S. PATENT DOCUMENTS 6,881,823 B2 * 4/2005 Ruben et al. ................. 530/324

FOREIGN PATENT DOCUMENTS

| | | |
|---|---|---|
| CA | 2624931 A1 | 4/2007 |
| JP | 11-29599 | 2/1999 |
| JP | 2004-057003 | 2/2004 |
| WO | 9900123 A1 | 1/1999 |
| WO | WO 2004050834 A2 * | 6/2004 |
| WO | 2005/110433 | 11/2005 |
| WO | 2006042242 A2 | 4/2006 |

OTHER PUBLICATIONS

Parameswaran et al. Trends in Biochemical Sciences, vol. 31(11), 2006, pp. 631-638.*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Lee et al (J Pharmacol Toxicol Methods. May-Jun. 2006;53(3):242-7. Epub Oct. 24, 2005).*
Shimosawa T. et al., "Adrenomedullin as a Potent Antioxidative and Antiatherosclerotic Substance," Drug News Perspect, (2005) pp. 185-189, 18:3.
Office Action issued to Chinese Application No. 200880117473.2; mailed Nov. 3, 2011.
Shindo et al, Hypotension and Resistance to Lipopolysaccharide-Induced Shock in Transgenic Mice Overexpressing Adrenomedullin in Their Vasculature, Circulation 2000; 101: 2309-2316.
Imai et al, Resistance to Neointimal Hyperplasia and Fatty Streak Formation in mice with Adrenomedullin Overexpression, Arterioscler Throm Vasc Biol. 2002; 22: 1310-1315.
Niu et al, Protective Effects of Endogenous Adrenomedullin on Cardiac Hypertrophy, Fibrosis, and Renal Damage, Circulation 2004; 109: 1789-1794.
Shindo et al, Vascular Abnormalities and Elevated Blood Pressure in Mice Lacking Adrenomedullin Gene, Circulation 2001:104: 1964-1971.
Kato et al, Plasma Levels of Adrenomedullin and Atrial and Brain Natriuretic Peptides in the General Population: Their Relations to Age and Pulse Pressure, Hypertension Res. 2002; 25: 887-892.

(Continued)

*Primary Examiner* — Brian J Gangle
*Assistant Examiner* — Andrea McCollum
(74) *Attorney, Agent, or Firm* — Hoffmann & Baron, LLP

(57) ABSTRACT

The object is to provide: a therapeutic or prophylactic agent for metabolic syndrome, which has improved stability in a living body; and others. The therapeutic or prophylactic agent for metabolic syndrome comprises, as an active ingredient, DNA that encodes receptor activity-modifying protein (RAMP) 2 and is selected from the items (a) to (d) below or a polypeptide encoded by the DNA: (a) DNA which has the nucleotide sequence depicted in SEQ ID NO:1; (b) DNA which has a nucleotide sequence capable of hybridizing with the nucleotide sequence depicted in SEQ ID NO:1 under stringent conditions; (c) DNA which has a nucleotide sequence encoding an amino acid sequence having the substitution, deletion and/or addition of one or more amino acid residues in the amino acid sequence depicted in SEQ ID NO:2; and (d) DNA which has a nucleotide sequence having a 90% or more homology with the nucleotide sequence depicted in SEQ ID NO:1.

1 Claim, 14 Drawing Sheets

(56) References Cited

OTHER PUBLICATIONS

Nambu et al, Expression of the adrenomedullin gene in adipose tissue, Regul Pept. 2005; 132: 17-22.
Parameswaran et al, RAMPS: the past, present and future, Trends in Biochemical Science, vol. 31, No. 11: 631-638, (2006).
Kogata et al, Cardiac Ischemia Activates Vascular Endothelial Cadherin Promoter in Both Preexisting Vascular Cells and Bone Marrow Cells Involved in Neovascularization, Circulation Research 2006; 98: 897-904.
Sohal et al, Temporally Regulated and Tissue-Specific Gene Manipulations in the Adult and Embryonic Heart Using a Tamoxifen-Inducible Cre Protein, Circulation Research 2001; 89: 20-25.
Tam et al, Enhanced Vascular Responses to Adrenomedullin in Mice Overexpressing Receptor-Activity-Modifying Protein 2, Circulation Research 2006; 98; 2: 262-270.
Tam et al, Effect of L-NAME on blood pressure regulation in mice overexpressing the adrenomedullin receptor component RAMP2, Acta Pharmacologica Sinica 2006, vol. 27, No. Suppl, 146-147.

Fukai et al, Concomitant expression of adrenomedullin and its receptor components in rat adipose tissues, Am J Physiol Endocrinol Metab 2005, 288, 1: E56-62.
Extended European Search Report issued to EP Application No. 08855467.0 on Apr. 8, 2011.
Fernandez-Sauze et al., "Effects of ardrenomedullin on endothelial cells in the multistep process of angiogenesis: Involvement of CRLR/RAMP2 and CRLR/RAMP3 receptors", International Journal of Cancer, vol. 108, No. 6, pp. 797-804 (2004).
Kamitani et al., "The RAMP2/CRLR complex is a functional ardrenomedullin receptor in human endothelial and vascular smooth muscle cells", FEBS Letters, vol. 448, No. 1, pp. 111-114 (1999).
Paulmyer-Lacroix et al., "Expression of adrenomedullin in adipose tissue of lean and obese women", European Journal of Endocrinology, vol. 155, No. 1, pp. 177-185, (2006).
Database GenBank [Online], XP002627124, (2010).
Kuwasako, Kenji et al., "The Function of Extracellular Cysteines in the Human Adrenomedullin Receptor", Hypertens. Res., vol. 26, Suppl. (2003), pp. S25-S31.

\* cited by examiner

HE STAIN

OIL RED O STAIN

RAMP2 EXPRESSION IN SINUSOIDAL EC

THERAPEUTIC OR PROPHYLACTIC AGENT, DETECTION METHOD AND DETECTION AGENT FOR METABOLIC SYNDROME, AND METHOD FOR SCREENING OF CANDIDATE COMPOUND FOR THERAPEUTIC AGENT FOR METABOLIC SYNDROME

TECHNICAL FIELD

The present invention relates to a therapeutic or prophylactic agent for metabolic syndrome, a test method, a test drug, and a screening method for candidate compounds for a therapeutic drug for metabolic syndrome.

BACKGROUND ART

In recent years, patients of metabolic syndrome have increased rapidly especially in advanced countries. Metabolic syndrome is a compound lifestyle disease where visceral fat type obesity (visceral obesity, abdominal obesity), and two or more of hyperglycemia, hypertension, and hyperlipidemia are combined. In accordance with such compound symptoms, a metabolic syndrome can accelerate the progression of heart disease, cerebral stroke or the like, and are the greatest cause of notable deterioration of the healthy lifespan and quality of life of the elderly. Under these circumstances, in order to maintain the vitality of society as a whole and reduce healthcare costs, there is a great social need for overcoming metabolic syndrome.

As an important molecular basis linking metabolic syndrome with arteriosclerosis, vascular complications, and organ dysfunction, humoral factors having various physiological functions such as adipokines have attracted attention. Humoral factors are produced in various peripheral organs besides the adipose tissue, and these peripheral organs closely cooperate via the humoral factors to maintain homeostasis in vivo, and on the other hand, a failure in the balance of the humoral factors is thought to contribute to arteriosclerosis and organ dysfunction. The present inventors have noted adrenomedullin (AM) and its receptor activity modifying protein (RAMP) system as one of such humoral factors.

Adrenomedullin (AM) is a peptide produced in the blood vessels and tissues of the whole body. It has become clear that AM has a variety of physiological functions including vasodilation function, fluid volume regulating function, hormone section regulation function, antioxidant function, antiinflammatory function and the like. The present inventors have thus far noted increased blood pressure in heterozygous AM knockout mice, and the aggravation of cardiac hypertrophy, fibrosis, nephropathy and arteriosclerosis, whereas AM-overexpressing mice were, on the contrary, recognized to have lower blood pressure and showed resistance to organ damages and arteriosclerosis; and thus reported that AM has an organ protective function, and antiarteriosclerotic function (refer to Non-Patent Documents 1 to 3).

Further, the present inventors were the first to clarify that AM is an essential molecule for blood vessel maturation and to stabilize the structure of blood vessels, through the observation that AM knockout mice were lethal at mid-gestation with severe hemorrhage and edema due to insufficient vascular development (refer to Non Patent Document 4). Moreover, it was recently reported that the AM concentration in blood elevates along with obesity and is correlated with the body mass index, and AM is expressed in adipose tissue, and this expression is upregulated with obesity conditions (refer to Non-Patent Documents 5 and 6). On the other hand, in AM knockout mice, with aging, along with obesity, glucose tolerance disorders and the aggravation of in vivo oxidative stress, the development of organ dysfunction was observed, suggesting a relationship between AM and metabolic syndrome.

[Non-Patent Document 1] T. Shindo et al., Circulation, 2000

[Non-Patent Document 2] Y. Imai, T. Sindo, et al., ATVB 2002

[Non-Patent Document 3] P. Niu, T. Shindo, et al., Circulation 2004

[Non-Patent Document 4] T. Shindo et al., Circulation 2001

[Non-Patent Document 5] J. Kato et al., Hypertens. Res. 2002

[Non-Patent Document 6] T. Nambu et al., Regul Pept. 2005

DISCLOSURE OF THE INVENTION

Problems to be Solved by the Invention

However, because AM has a short half life in blood, it is subject to many constraints for the use as a therapeutic drug for metabolic syndrome which is a chronic malady.

The present invention was made in consideration of the above circumstances, and has the objective of providing a therapeutic or prophylactic agent for metabolic syndrome for which in vivo stability can be improved. Further, the present invention also has the objective of providing a test method and test drug for metabolic syndrome, and a screening method for candidate compounds for a therapeutic drug for metabolic syndrome.

Means for Solving the Problems

The present inventors, through a process of carrying out diligent research, attained note of the receptor system of AM. The AM receptor itself is a seven-transmembrane domain receptor called CRLR (calcitonin receptor-like receptor) belonging to the G protein-coupled type receptors, class B. CRLR binds to any of the RAMP (receptor activity modifying protein) 1, 2, and 3 subisoforms which are one-transmembrane domain proteins, and forms a heterodimer.

The present inventors, by suitably modifying the subisoform of the RAMP binding to the CRLR, discovered that the affinity to AM receptor and ligands can be controlled, thus completing the present invention. Specifically, the present invention provides the following.

The first aspect of the present invention is a therapeutic or prophylactic agent for metabolic syndrome comprising as an effective component a DNA described in any one of (a) to (d) below, encoding receptor activity modifying 2 (RAMP2) protein, or a polypeptide encoded by the DNA;

(a) a DNA having a base sequence described in SEQ. ID. No. 1;

(b) a DNA having a base sequence which is capable of hybridizing under stringent conditions with the base sequence described in SEQ. ID. No. 1;

(c) a DNA having a base sequence encoding an amino acid sequence wherein, in the amino acid sequence described in SEQ. ID. No. 2, one or a plurality of amino acids are substituted, eliminated, and/or added;

(d) a DNA consisting of a base sequence having a homology of 90% or more with the base sequence described in SEQ. ID. No. 1.

The second aspect of the present invention is a test method for metabolic syndrome comprising:

an extraction step of extracting DNA from a cell of a test subject;

an amplification step of carrying out a polymerase chain reaction using a primer which is capable of selectively amplifying a DNA consisting of the base sequence described in SEQ. ID. No. 3 or part of or all of a DNA of its expression control region, with the extracted DNA as a template;

a determination step of determinating a base sequence of the amplified DNA; and a comparison step of comparing the determined base sequence with the base sequence described in SEQ. ID. No. 3.

The third aspect of the present invention is a test drug for metabolic syndrome comprising as an effective component a primer which is capable of selectively amplifying a DNA consisting of the base sequence described in SEQ. ID. No. 3 or part of or all of a DNA of its expression control region; or an antibody or antibody fragment which selectively binds to a polypeptide consisting of an amino acid sequence described in SEQ. ID. No. 2.

The fourth aspect of the present invention is a screening method for candidate compounds for a therapeutic drug for metabolic syndrome, comprising:

a step of bringing into contact a test substance and a polypeptide having an amino acid sequence described in SEQ. ID. No. 2, or an amino acid sequence wherein, in the amino acid sequence described in SEQ. ID. No. 2, one or a plurality of amino acids are substituted, eliminated, and/or added; and a step of detecting binding between the polypeptide and the test substance.

The fifth aspect of the present invention is a screening method for candidate compounds for a therapeutic drug for metabolic syndrome comprising:

a step of administering a test substance to an animal wherein an endogenous RAMP2 gene has been mutated or knocked out; and a step of detecting improvement of symptoms of metabolic syndrome.

The sixth aspect of the present invention is a screening method for candidate compounds for a therapeutic drug for metabolic syndrome, comprising:

a step of bringing into contact a test substance and a cell expressing a DNA having a base sequence described in SEQ. ID. No. 1, a DNA having a base sequence which is capable of hybridizing under stringent conditions with the base sequence described in SEQ. ID. No. 1, or a DNA consisting of a base sequence having a homology of 90% or more with the base sequence described in SEQ. ID. No. 1, and a step of detecting changes in an expression amount of the DNA.

The seventh aspect of the present invention is a screening method for candidate compounds for a therapeutic drug for metabolic syndrome, comprising:

a step of bringing into contact a test substance and a cell expressing a DNA having a base sequence described in SEQ. ID. No. 1, a DNA having a base sequence which is capable of hybridizing under stringent conditions with the base sequence described in SEQ. ID. No. 1, or a DNA consisting of a base sequence having a homology of 90% or more with the base sequence described in SEQ. ID. No. 1, and a step of detecting changes in intracellular localization of a protein synthesized from the DNA.

The eighth aspect of the present invention is a screening method for candidate compounds for a therapeutic drug for metabolic syndrome, comprising:

a step of bringing into coexistence a test substance; a polypeptide having an amino acid sequence described in SEQ. ID. No. 6, or an amino acid sequence wherein, in the amino acid sequence described in SEQ. ID. No. 6, one or a plurality of amino acids are substituted, eliminated, and/or added; and an enzyme which is capable of decomposing this polypeptide;

a step of measuring a residue of the polypeptide after a predetermined period; and a step of comparing the measured value of the residue and a residue measured in an absence of the test substance.

The ninth aspect of the present invention is a screening method for candidate compounds for a therapeutic drug for metabolic syndrome comprising:

a step of bringing into contact a test substance and a cell expressing a DNA having a base sequence described in SEQ. ID. No. 1, a DNA having a base sequence which is capable of hybridizing under stringent conditions with the base sequence described in SEQ. ID. No. 1, or a DNA consisting of a base sequence having a homology of 90% or more with the base sequence described in SEQ. ID. No. 1, and a DNA having a base sequence described in SEQ. ID. No. 4, a DNA having a base sequence which is capable of hybridizing under stringent conditions with the base sequence described in SEQ. ID. No. 4, or a DNA consisting of a base sequence having a homology of 90% or more with the base sequence described in SEQ. ID. No. 4; and a step of detecting induction of intracellular signal transmission based on a stimulus of a ligand encoded by a DNA having a base sequence described in SEQ. ID. No. 5, or activation of G protein based on a stimulus of the ligand.

Effects of the Invention

According to the present invention, it is possible to effectively treat or prevent metabolic syndrome because RAMP2 or its functional equivalent substance is provided in the body. Moreover, because RAMP2 and its functional equivalent substance are membrane proteins, they have a long half life in the blood, and their stability in the body can be improved.

BRIEF DESCRIPTION OF THE DRAWINGS

FIGS. 3(a), 3(b), 3(c), 3(d), 3(e), and 3(f) are all

PREFERRED MODE FOR CARRYING OUT THE INVENTION

Figure 1A:
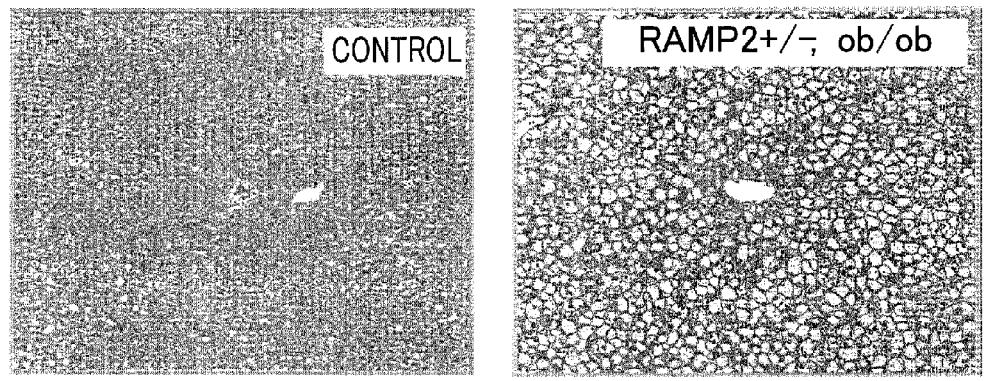
FIG. 1(a) is a photograph of HE stain and 1(b) is a photograph of oil red 0 stain of the liver harvested from a RAMP2+/−, ob/ob mouse.

An embodiment of the present invention is explained below.

Therapeutic Drug•Prophylactic Drug

The therapeutic or prophylactic drug for metabolic syndrome of the present invention comprises as an effective component a DNA described in any of (a) to (d) below, encoding a receptor activity modifying 2 (RAMP2) protein, or a polypeptide encoded by the DNA.

(a) a DNA having a base sequence described in SEQ. ID. No. 1;

(b) a DNA having a base sequence which is capable of hybridizing under stringent conditions with the base sequence described in SEQ. ID. No. 1;

(c) a DNA having a base sequence encoding an amino acid sequence wherein, in the amino acid sequence described in SEQ. ID. No. 2, one or a plurality of amino acids are substituted, eliminated, and/or added;

(d) a DNA consisting of a base sequence having a homology of 90% or more with the base sequence described in SEQ. ID. No. 1.

Further, in the present specification, "metabolic syndrome" indicates a condition wherein visceral fat type obesity (visceral obesity, abdominal obesity) and two or more of hyperglycemia, hypertension, hyperlipidemia are combined, and includes complications of arteriosclerosis, ischemic ailments (myocardial infarction, angina pectoris, stroke, arteriosclerosis obliterans), blood vessel failure, organ dysfunction and the like, or is assumed to be one cause of these complications.

In the present invention "DNA" may be either of the sense strand or the antisense strand (for example, it can be used as a probe), and its form may be either a single strand or a double strand. Further, it may be a genome DNA, it may be a cDNA, or it may be a synthesized DNA.

The most preferable state of the DNA of the present invention is a DNA having the base sequence described in SEQ. ID. No. 1, but the DNA of the present invention further includes various mutations and homologues having a therapeutic or prophylactic effect for metabolic syndrome. Here, "therapeutic or prophylactic effect for metabolic syndrome" is an effect where at least one type of symptom of visceral fat type obesity (visceral obesity, abdominal obesity), hyperglycemia, hypertension, and hyperlipidemia is improved, or worsening of the symptoms is suppressed, and indicates an effect where the improvement or suppression is statistically significant.

SEQ. ID. No. 1 is a base sequence encoding the extracellular domain of human RAMP2. Mutants or homologues of the DNA having this base sequence described in SEQ. ID. No. 1, for example, include DNA having a base sequence capable of being hybridized under stringent conditions with the base sequence described in SEQ. ID. No. 1. Herein, as the "stringent conditions", for example, there can be mentioned conditions wherein in a normal hybridization buffer solution, reaction is carried out at 40 to 70° C. (preferably 60 to 65° C.), and washing in a washing solution with a salt concentration of 15 to 300 mM (preferably 15 to 60 mM).

Further, it is known that SEQ. ID. No. 2 constitutes the extracellular domain of the human RAMP2 protein (Trends in Biochemical Science, Vol. 31, No. 11, pp. 631-638). This also includes DNA having a base sequence encoding an amino acid sequence wherein, in the amino acid sequence described in SEQ. ID. No. 2, one or a plurality of amino acids are substituted, eliminated and/or added. Herein, "one or a plurality of" is usually 50 amino acids or less, preferably 30 amino acids or less, and more preferably 10 amino acids or less (for example, 5 amino acids or less, 3 amino acids or less, 1 amino acid). In the case of maintaining the ability to activate muscle specific tyrosine kinase, it is desirable that in the mutated amino acid residue, the properties of the amino acid side chain be preserved, and other amino acids be mutated. For example, as the properties of the amino acid side chain, it is possible to mention hydrophobic amino acids (A, I, L, M, F, P, W, Y, V), hydrophilic amino acids (R, D, N, C, E, Q, G, H, K, S, T), amino acids having aliphatic side chains (G, A, V, L, I, P), amino acids having hydroxyl group-containing side chains (S, T, Y), amino acids having sulfur atom-containing side chains (C, M), amino acids having carboxylic acid and amide-containing side chains (D, N, E, Q), amino acids having base-containing side chains (R, K, H), and amino acids having aromatic side chains (H, F, Y, W) (the parenthesis all show the one letter designations of amino acids).

It is known that for a protein having an amino acid sequence modified such that one or a plurality of amino acids are eliminated, added and/or substituted with another amino acid, the biological activity can be maintained (Mark, D. F. et al, Proc. Natl. Acad. Sci. USA (1984) 81, pp. 5662-5666; Zoller, M. J. & Smith, M., Nucleic Acids Research (1982) 10, pp. 6487-6500; Wang A. et al., Science 224 pp. 1431-1433; Dalbadie-McFarland G. et al., Proc. Natl. Acad. Sci. USA (1982) 79, pp. 6409-6413).

Furthermore, a mutant or homologue of DNA having the base sequence described in SEQ. ID. No. 1 includes DNA consisting of a base sequence having a high homology with the base sequence described in SEQ. ID. No. 1. Such a DNA has a homology of preferably 90% or more, and more preferably 95% or more (96% or more, 97% or more, 98% or more, 99% or more). The homology of an amino acid sequence or a base sequence can be determined according to the BLAST algorithm by Karlin and Altschul (Proc. Natl. Acad. Sci. USA 90: 5873-5877, 1993). Based on this algorithm, the programs called BLASTN and BLASTX have been developed (Altschul et al., J. Mol. Biol. 215: 403-410, 1990). In the case of analysis of a base sequence according to the BLASTN algorithm based on BLAST, the parameters are set to, for example, score=100, wordlength=12. Further, in the case of analysis of an amino acid sequence according to the BLASTX algorithm based on BLAST, the parameters are set to, for example, score=50, wordlength=3. In the case of using the BLAST and Gapped BLAST programs, the default parameters of each program are used. The specific techniques of these analysis methods are publicly known (http://www.ncbi.nlm.nih.gov).

The method for acquiring the DNA of the present invention is not particularly limited, and a publicly known method method such as a method of obtaining cDNA by reverse transcription from mRNA (for example, the RT-PCR method), method of modification from a genome DNA, method of synthesis by chemical synthesis, and method of isolating from a genome DNA library or cDNA library or the like can be mentioned (for example, refer to Japanese Unexamined Patent Publication No. Hei 11-29599).

Polypeptide

The polypeptide used as a therapeutic or prophylactic agent in the present invention is encoded by the previously described DNA, and for example, has an amino acid sequence described in SEQ. ID. No. 2, or an amino acid sequence wherein, in the amino acid sequence described in SEQ. ID. No. 2, one or a plurality of amino acids are substituted, eliminated and/or added.

The above described polypeptide, because it does not have all of the transmembrane region or intracellular domain of the human RAMP 2 protein, is expected to be endowed with a high solubility, and can be easily purified by the following method, or the like. Further, the extracellular domain of RAMP2 is understood to be indispensable because it binds to CRLR and forms a complex (data not shown). Because of this, the above described polypeptide forms a complex with CRLR on the cell membrane to which it is administered, and exhibits therapeutic or prophylactic effects for metabolic syndrome.

The polypeptide encoding the DNA of the present invention can be manufactured using a transformant into which is introduced an expression vector including the above described DNA, for example. Namely, first, this transformant is cultured under appropriate conditions, and a protein (polypeptide) encoding this DNA is synthesized. Then, by retrieving the synthesized protein from the transformant or the culture fluid, the polypeptide of the present invention can be obtained.

The culture of the transformant, in order to make it possible to obtain the polypeptide in large quantities and easily, is appropriately selected from the publicly known nutrient culture media according to the type and the like of the transformant, and it is possible to carry out appropriate adjustment of the temperature, the pH of the nutrient culture media, culture time and the like (for example, refer to Japanese Unexamined Patent Publication No. Hei 11-29599).

The isolation method and purification method of the polypeptide are not particularly limited, and a publicly known method such as a method utilizing solubility, a method utilizing differences in molecular weight, a method utilizing electric charge and the like can be mentioned (for example, refer to Japanese Unexamined Patent Publication No. Hei 11-29599). Further, the vector and transformant which can be used in the present invention are explained below.

Vector

The expression vector can be manufactured by inserting the above described DNA into an appropriate vector. The "appropriate vector" may be a prokaryote or eukaryote capable of reproduction within a host or self-reproduction, and may be appropriately selected in response to the target use. For example, in the case that it is desired to obtain a large amount of DNA, a high copy vector may be selected, and in the case that it is desired to obtain a polypeptide, an expression vector may be selected. Specific examples of these are not particularly limited, and for example, the publicly known vectors described in Japanese Unexamined Patent Publication No. Hei 11-29599 can be mentioned.

Transformant

The transformant can be manufactured by introducing a vector containing the above described DNA into a host. Such a host may be one which is compatible with the vector of the present invention and is transformed, and specific examples thereof are not particularly limited, but publicly known natural cells such as bacteria, yeast, zooblasts, insect cells and the like, and artificially established cells (refer to Japanese Unexamined Patent Publication No. Hei 11-29599) can be mentioned.

The insertion method of the vector may be appropriately selected according to the type and the like of the vector and the host. Specific examples thereof are not particularly limited, but publicly known methods such as the protoplast method and competent method (for example, refer to Japanese Unexamined Patent Publication No. Hei 11-29599) can be mentioned.

The "effective component" in the present specification indicates a component contained in an amount necessary in order to obtain a therapeutic or prophylactic effect for metabolic syndrome, and other components may also be contained so long as the effect is not degraded to below the desired level. Further, the route of administration of the pharmaceutical composition may be either oral or parenteral, and is established as appropriate.

In the case of oral administration, the pharmaceutical composition may contain additives such as the generally used bonding agents, covering agents, fillers, lubricants, disintegrators, and humectants, and may be formulated in a variety of forms such as pills, granules, subtle granules, powders, capsules and the like. Further, the pharmaceutical composition may also be in a liquid state such as an internal solution, suspension, emulsion syrup and the like, and may be in a dry state which is redissolved upon use.

In the case of parenteral administration, the pharmaceutical composition may contain additives such as stabilizers, buffers, preservatives, tonicity adjustment agents and the like, and may usually be distributed in a state accommodated in a unit dose ampule, multiple dose container or a tube. Further, the pharmaceutical composition may be formulated as a powder which is resoluble in a suitable carrier (sterile water or the like) at the time of use.

Test Method, Test Drug

The above described DNA can be utilized in a test for the presence or absence of an affliction of metabolic syndrome. The test method for metabolic syndrome according to the present invention includes an extraction step, amplification step, determination step and comparison step.

In the extraction step, DNA is extracted from a cell of the test subject. The extraction technique may follow the usual methods.

The amplification step carries out a polymerase chain reaction using a primer which is capable of specifically amplifying a DNA consisting of the base sequence described in SEQ. ID. No. 3, or part or all of a DNA of its expression control region, with the extracted DNA as a template. In this way, a DNA having part or all of the SEQ. ID. No. 3 is specifically amplified. Further, SEQ. ID. No. 3 is the full base sequence of the human RAMP2 gene.

In the determination step, the base sequence of the amplified DNA is determined, and in the comparison step, the determined base sequence is compared with the base sequence of SEQ. ID. No. 3. The determination and comparison of the base sequence may follow the usual methods. As the results of the comparison, it can be judged that if the base sequence of the acquired DNA differ from SEQ. ID. No. 3, the test subject is already afflicted with metabolic syndrome, or could easily become afflicted.

Further, in the test method of the present invention it is also possible to further apply, for example, a judgment step wherein it is judged whether or not the symptoms relating to metabolic syndrome are improved or their worsening is suppressed, when the DNA amplified in the amplification step is introduced into a cell, tissue, organ or individual where the RAMP2 has been mutated or knocked out. In this way, the test accuracy can be improved because it is possible to exclude cases wherein the differences between the base sequence of the amplified DNA and the base sequence of SEQ. ID. No. 1 are simply polymorphism.

Knockout Body

By mutating or knocking out the above described DNA, it is possible to manufacture a nonhuman transformed cell, tissue, organ or individual. The nonhuman animal is not particularly limited, but a mouse, rat, guinea pig, hamster, rabbit, goat, pig, dog, cat and the like can be mentioned.

The manufacturing method of the nonhuman transformed animal is, for example, as follows. First, the DNA, DNA mutation, or DNA homologous recombination of the DNA of the present invention, is introduced into a fertilized egg of a nonhuman mammal. Then, this fertilized egg is transplanted to a female individual's womb and allowed to develop, and in this way the DNA of the present invention can manufacture a transformed nonhuman transformed animal.

The manufacture of a nonhuman transformed animal can, more specifically, be carried out as follows. First, a female individual made to superovulate by hormone administration is cross bred with a male. Next, a fertilized egg is extracted from the oviduct of the female individual one day after the cross breeding, and a vector including the mutated DNA or DNA which can be homologously recombined with the DNA is introduced by the microinjection method or the like into the fertilized egg. Then, after incubating the fertilized egg after the introduction by an appropriate method, a viable fertilized egg is transplanted to the uterus of a female individual (adoptive parent) made to have a false pregnancy, and a newborn is delivered. It can be confirmed by Southern analysis whether the DNA in this newborn is transformed by extracting DNA from a cell of this newborn.

In addition, a nonhuman transformed animal may be manufactured by carrying out gene introduction and selection in an embryonic stem cell (ES cell) line, then manufacturing a chimera animal to which the germ cell line is contributed, and cross breeding.

Another detection method includes a detection step for detecting an expression amount of DNA having the base sequence described in SEQ. ID. No. 1 in a cell derived from the test subject, and a comparison step for comparing the expression amount of the detected DNA and the expression amount of the DNA described in SEQ. ID. No. 1 of a healthy person.

Herein, the "DNA expression" includes the transcription level (expression of mRNA) and the translation level (expression of protein). Accordingly, the expression amount my be detected by carrying out quantitative RT-PCR using a primer which is capable of specifically amplifying DNA having part of all of the base sequence described in SEQ. ID. No. 1, or detected by carrying out by Western analysis or the like using an antibody or an antibody fragment specifically binding to a polypeptide consisting of the amino acid sequence described in SEQ. ID. No. 2.

According to these detection methods, in the comparison results, in the case that the expression amount of DNA in the test subject differs significantly from the expression amount of the DNA in a healthy person, it can be judged that the test subject is already afflicted with metabolic syndrome, or could easily become afflicted.

The test drug for metabolic syndrome according to the present invention contains as an effective component a primer which is capable of specifically amplifying DNA having part or all of the base sequence described in SEQ. ID. No. 1, or the above described antibody or antibody fragment.

Screening Method

The screening method for candidate compounds for therapeutic drugs for metabolic syndrome according to the present invention includes a step of administering a test substance to an animal where the endogenous RAMP2 gene has been knocked out, and a step for detecting symptom improvement of metabolic syndrome.

According to this screening method, a test substance for which symptom improvement is detected can complement or substitute the function of RAMP2, and thus it can be specified as a candidate compound for a therapeutic drug for metabolic syndrome.

Another screening method includes a step of bringing into contact the test substance and a cell expressing a DNA having the base sequence described in SEQ. ID. No. 1, a DNA having a base sequence which can hybridize under stringent conditions with the base sequence described in SEQ. ID. No. 1, or a DNA consisting of a base sequence having a homology of 90% or more with the base sequence described in SEQ. ID. No. 1; and a step of detecting changes in the expression amount of this DNA.

The test substance for which changes in the expression amount of the DNA described in SEQ. ID. No. 1 are detected is conjectured to be capable of strengthening or decreasing the functioning of RAMP2. Specifically, a substance, which increases the DNA expression level, can strengthen the functioning of RAMP2, and thus is conjectured to be capable of treating metabolic syndrome when administered. On the other hand, a substance which decreases the DNA expression amount is capable of decreasing the functioning of RAMP2, and thus it is conjectured that metabolic syndrome can be treated by administering a substance which inhibits this substance.

Further, the cell used in this method and in the below described method may be one in which endogenous RAMP2 is expressed, or not expressed. However, a cell which does not express endogenous RAMP2 (for example, COS7) is preferable in the point that it is possible to exclude unclear influence due to the endogenous RAMP2.

Another screening method includes a step of bringing into contact the test substance and a polypeptide having the amino acid sequence described in SEQ. ID. No. 2, an amino acid sequence wherein, in the amino acid sequence described in SEQ. ID. No. 2, one or a plurality of amino acids are substituted, eliminated, and/or added; and a step of detecting binding between the polypeptide and the subject substance.

According to this screening method, a test substance binding to the polypeptide of SEQ. ID. No. 2 and the like can be obtained. Such a test substance has the possibility of participating in the therapeutic pathway of metabolic syndrome via the polypeptide of SEQ. ID. No. 2 and the like, and is conjectured to be capable of treating metabolic syndrome.

Another screening method includes a step of bringing into contact the test substance and a cell expressing DNA having the base sequence described in SEQ. ID. No. 1, DNA having a base sequence capable of hybridizing under stringent conditions with the base sequence described in SEQ. ID. No. 1, or a DNA consisting of a base sequence having a homology of 90% or more with the base sequence described in SEQ. ID. No. 1; and a step of detecting changes in the intracellular localization of a protein synthesized from said DNA.

According to this screening method, it is possible to obtain a test substance which changes the intracellular localization of a protein synthesized from the SEQ. ID. No. 1 or the like. Here, the RAMP2 is first binded to AM and a receptor, and then is taken into the cell by endocytosis along with the receptor, and if there is no stimulus to the AM from the outside, as long as the cell is alive, it will be stably present on the cell membrane. Further, even if it temporarily taken into the cell temporarily by endocytosis, part of it again returns to the cell membrane and is conjectured to be recycled. Accordingly, the obtained test substance has the possibility of improving the therapeutic effects of metabolic syndrome via RAMP2, and can be anticipated as a therapeutic drug for metabolic syndrome.

Another screening method includes a step of bringing into coexistence the test substance; a polypeptide having the amino acid sequence described in SEQ. ID. No. 6, or an amino acid sequence wherein, in the amino acid sequence described in SEQ. ID. No. 6, one or a plurality of amino acids are substituted, eliminated, and/or added; and an enzyme capable of decomposing this polypeptide; a step of measuring the residue of the polypeptide after a predetermined period of time; and a step of comparing with a residue measured in the absence of the test substance before the measurement of the residue.

SEQ. ID. No. 6 is the full amino acid sequence of human adrenomedullin (AM). According to this screening method, it is possible to obtain a substance expected to change the in vivo stability of a polypeptide (AM or the like) having the amino acid sequence described in SEQ. ID. No. 6 or the like. Such a substance has the possibility of improving the therapeutic effects of metabolic syndrome via RAMP2, and may be anticipated as a therapeutic drug of metabolic syndrome. Further, the enzyme used in this method may be specific or non-specific to the above polypeptide, and for example may be endopeptidase.

Another screening method includes a step of bringing into contact the test substance and a cell expressing the DNA having the base sequence described in SEQ. ID. No. 1, DNA having a base sequence which is capable of hybridizing under stringent conditions with the base sequence described in SEQ. ID. No. 1, or a DNA consisting of a base sequence having a homology of 90% or more with the base sequence described in SEQ. ID. No. 1, and DNA having the base sequence described in SEQ. ID. No. 4, DNA having a base sequence which is capable of hybridizing under stringent conditions with the base sequence described in SEQ. ID. No. 4, or a DNA consisting of a base sequence having a homology of 90% or more with the base sequence described in SEQ. ID. No. 4; and a step of detecting induction of intracellular signal transmission based on a stimulus of a ligand encoded by the DNA having the base sequence described in SEQ. ID. No. 5, or activation of the G protein based on a stimulus of the ligand.

SEQ. ID. No. 4 is an amino acid sequence constituting the seven-transmembrane domain receptor called CRLR (calcitonin receptor-like receptor) belonging to the G protein coupled receptors, class B. Further, SEQ. ID. No. 5 is the full base sequence of the human RAMP2 gene.

According to this screening method, it is possible to obtain a substance which induces intracellular signal transmission based on an AM stimulus, or activates the G protein, in a cell coexpressing RAMP2 and CRLR. Such a substance has the possibility of improving the therapeutic effects of metabolic syndrome by RAMP2, via the induction of intracellular signal transmission, or activation of the G protein, and can be anticipated as a therapeutic drug for metabolic syndrome.

Further, the induction of intracellular signal transmission can be detected by indicators of changes (especially increases) of the level of intracellular cAMP, Ca, NO, the activity level of PKA, the phosphorylation level of Akt, ERK, P38MAPK, PI3K and the like.

Another screening method includes the step of specifying the steric constitution of the binding pocket which is formed by a complex of a polypeptide having an amino acid sequence wherein in the amino acid sequence described in SEQ. ID. No. 2, one or a plurality of amino acids are substituted, eliminated and/or added, and a polypeptide having an amino acid sequence wherein in the amino acid sequence described in SEQ. ID. No. 5, one or a plurality of amino acids are substituted, eliminated and/or added; and a step of classifying on a computer from a previously known structure library a substance predicted to be able to bind via the binding pocket with the complex based on the steric structure.

According to this screening method, it is possible to greatly narrow down from an enormous number of substances, candidates which are able to bind to a complex of RAMP2 and CRLR. By further limiting the narrowed down candidates using one of the above described screening methods, it is possible to further anticipate as a therapeutic drug for metabolic syndrome one having a high possibility of improving the therapeutic effects of metabolic syndrome by RAMP2. Further, the steps themselves of this in silico screening method may be carried out according to the usual methods.

EXAMPLES

Example 1

Manufacture of a RAMP2 Gene Knockout Mouse

A targeting vector was manufactured by the following procedure. Namely, from among the genome DNA sequence including RAMP2, as a homologous sequence of the 5' side, a sequence of approximately 3 kb including from the upstream of the exon 1 of RAMP2, to midway of the intron 1 is synthesized by PCR (5' homology arm), and as a homologous sequence of the middle, from midway of the intron 1 to downstream of exon 4 was synthesized by PCR (loxP arm), and as a homologous sequence of the 3' side, a sequence of approximately 3 kb downstream of exon 4 was synthesized by PCR (3' homology arm).

Next, by subcloning at pBluescript, in order from the 5' side in the direction of the 3' side, the 5' homology arm, loxP, loxP arm, the sequence of the neomycin resistance gene (pGK-neo), loxP, and the 3' homology arm, the targeting vector was manufactured. Namely, exons 2 to 4 of RAMP2 are set to be held between two loxP sites.

After making the obtained targeting vector linear by restriction enzyme treatment, it was introduced into a mouse ES cell by electroporation. The ES cell clones where recombination occurred were concentrated with neomycin resistance as an indicator, and further, the homolog recombinant ES cells were selected by Southern blotting.

By microinjecting the selected ES cells into mouse blastocyst, a chimera mouse was manufactured. This chimera mouse was cross bred with a wild type mouse, and a mouse where the loxP site was introduced at the intron 1 and downstream of the exon 4 of the RAMP2 gene in one of the genome sequences (hetero flox mouse) was manufactured.

By cross breeding the manufactured hetero flox mouse with a mouse which expresses the Cre recombinase gene under a CAG promoter (CAG-Cre mouse), a RAMP2 hetero knockout mouse in which the domain held between the loxP was removed was obtained. By cross breeding these RAMP2 hetero knockout mice among themselves, RAMP2 homo knockout mice were obtained.

Experiment 2

Cross Breeding of Genetically Obese Mice

By cross breeding the RAMP2 hetero knockout mouse (RAMP2+/−) obtained in Experiment 1 with a leptin deficient (ob/ob) mouse which is a genetically obese mouse, and by back crossing the offspring generation mice (RAMP2+/−, wt/ob) with ob/ob mice, grandchild generation mice (RAMP2+/−, ob/ob) were manufactured.

The ob/ob mice displayed symptoms of obesity, but the RAMP2+/−, ob/ob mice displayed more severe symptoms of obesity. This result suggests that reduced expression of RAMP2 is a cause of worsening of obesity symptoms.

Experiment 3

Fatty Liver

Figure 1B:
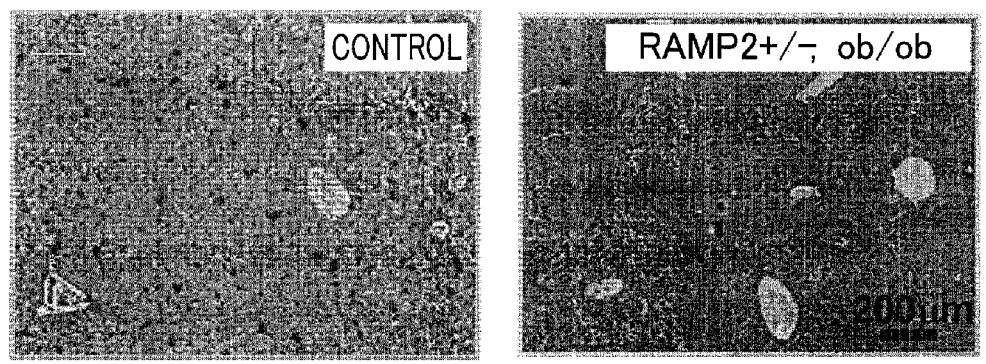

Livers were harvested from an ob/ob mouse and RAMP2+/−, ob/ob mouse, and slices thereof were stained. FIG. 1(a) shows a photograph of hematoxylin eosin (HE) staining, and FIG. 1(b) shows a photograph of oil red O staining.

As shown in FIG. 1(a), in a RAMP2+/−, ob/ob mouse, the white flecks of fat drops were observed over a remarkably wider range than in the ob/ob mouse. This result is consistent with the result of FIG. 1(b) where an image of far stronger redness by fat drop staining was obtained in the RAMP2+/−, ob/ob mouse than in the ob/ob mouse. From these results, it is indicated that reduced expression of RAMP2 is a cause of worsened symptoms of fatty liver.

Experiment 3

Arteriosclerosis

Morphology

Figure 2A:
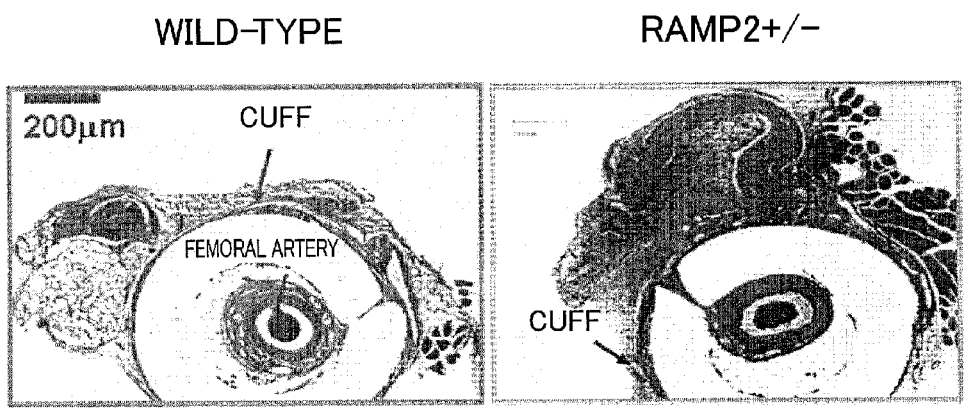
FIG. 2 (a) is a photograph of a slice of the femoral artery and its surroundings, of a RAMP2+/− mouse, and 2(b) an enlargement of a portion of the femoral artery.
Figure 2B:
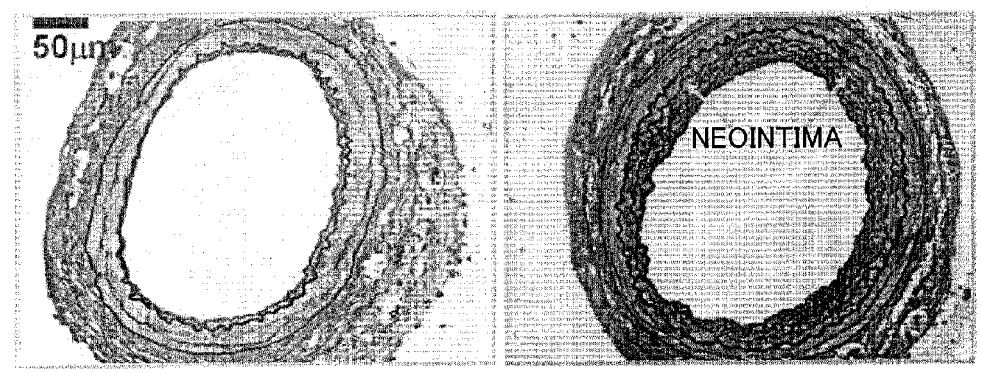

Arteriosclerosis was induced by indwelling for four weeks of a cuff of a polyethylene tube surrounding the femoral artery of a RAMP2 hetero knockout mouse (RAMP2+/−) obtained in Experiment 1, and a wild type mouse (RAMP2+/+). FIG. 2(a) shows a photograph at low magnification of a sample slice of the cuff indwelling portion, stained by elastic Van Gieson staining, and FIG. 2(b) shows a magnified photograph of the femoral artery.

As shown in FIG. 2(a), compared to the wild type mouse, the RAMP2+/− mouse showed enhanced proliferation of smooth muscle cells, infiltration of inflammatory cells, and accumulation of extracellular matrix. Further, as shown in FIG. 2(b), compared to the wild type mouse, the RAMP2+/− mouse was observed to have notable formation of a neointima at the blood vessel lumen. According to the above results, it can be judged that, compared to a wild type mouse, a RAMP2+/− mouse has far worse arteriosclerosis from a morphological viewpoint.

Immunology

In order to confirm the results of FIG. 2 from the viewpoint of immunology, the expression of the ICAM1, VCAM1, MCP1, and PCNA proteins in the femoral artery of the mouse after the indwelling in Experiment 3 were studied. Specifically, using the antibodies binding to each protein, the femoral artery was immunostained according to the usual methods, and the results are shown in FIGS. 3(a) to (d).

As shown in FIGS. 3(a) to (d), all of ICAM1, VCAM1, MCP1 and PCNA are expressed in notably greater amounts in the RAMP2+/− mouse than in a wild type mouse.

ICAM1 and VCAM1 are adhesion molecules, which show enhanced expression along with tissue inflammation, and thus suggest that stronger inflammation arises in a RAMP2+/− mouse than in a wild type mouse. This can be supported by the observation that the expression of MCP1, a chemokine, is more enhanced in a RAMP2+/− mouse than in a wild type mouse.

Further, PCNA is a marker of proliferating cells, thus it was confirmed that the proliferation of smooth muscle cells is more enhanced in the RAMP2+/− mouse than in the wild type mouse.

Figure 3:
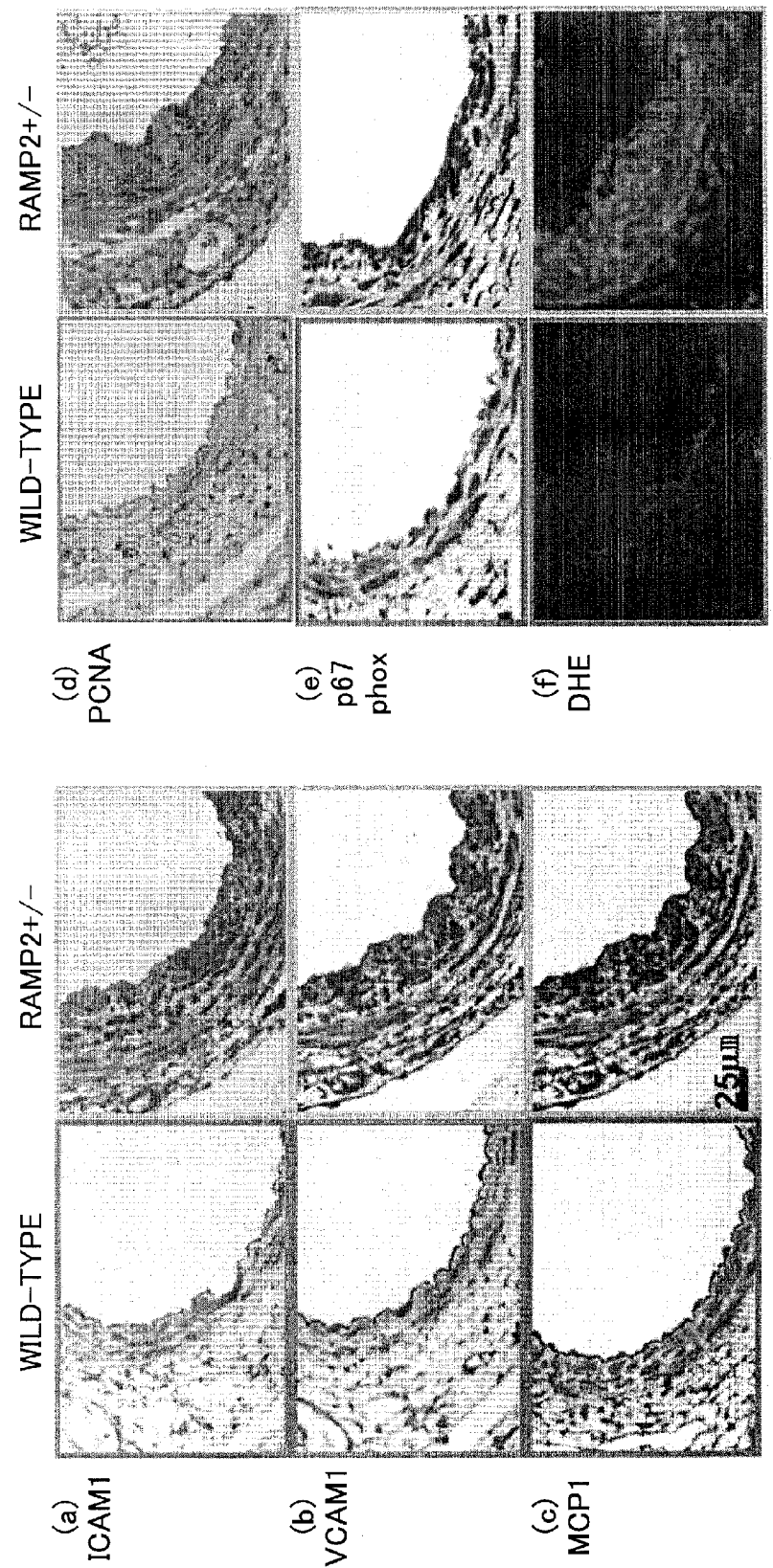
FIG. 3 is a femoral artery sectional photographs of a RAMP2+/− mouse.

FIG. 3(f) is a photograph of a dihydroethidium (DHE)—stained slice of a femoral artery of the mouse after indwelling, and FIG. 3(e) is a photograph of an immunostained slice of the femoral artery by p67phox antibody.

As shown in FIG. 3(f), the staining of the red color indicates the presence of a superoxide, and in the RAMP2+/− mouse, compared to the wild type mouse, this was observed over a far wider range and more strongly. In this way, it was confirmed that in a RAMP2+/− mouse, the oxidative stress at the pathologically changed portions was more enhanced than in the wild type mouse.

On the other hand, as shown in FIG. 3(e), p67phox was expressed in a notably greater level in a RAMP2+/− mouse than in a wild type mouse. Based on p67phox being a subunit of NADPH oxidase, which participates in the production of active oxygen, it is suggested that enhanced NADPH oxidase activity is a cause of the enhanced oxidative stress in pathologically changed portions.

According to the above results, it was judged that in a RAMP2+/− mouse, compared to a wild type mouse, arteriosclerosis is notably worsened also from the viewpoint of immunology.

Molecular Genetics

In the above described mouse before and after indwelling, the expression of RAMP2, RAMP3, CRLR and AM were studied. First, tissue was harvested from the vicinity of the femoral artery from a mouse before and after indwelling, and with total RNA extracted from this tissue as a template, quantitative real time PCR was carried out using a primer of a sequence specific to each gene. The specific process was according to the usual method. The results are shown in FIG. 4.

Figure 4:
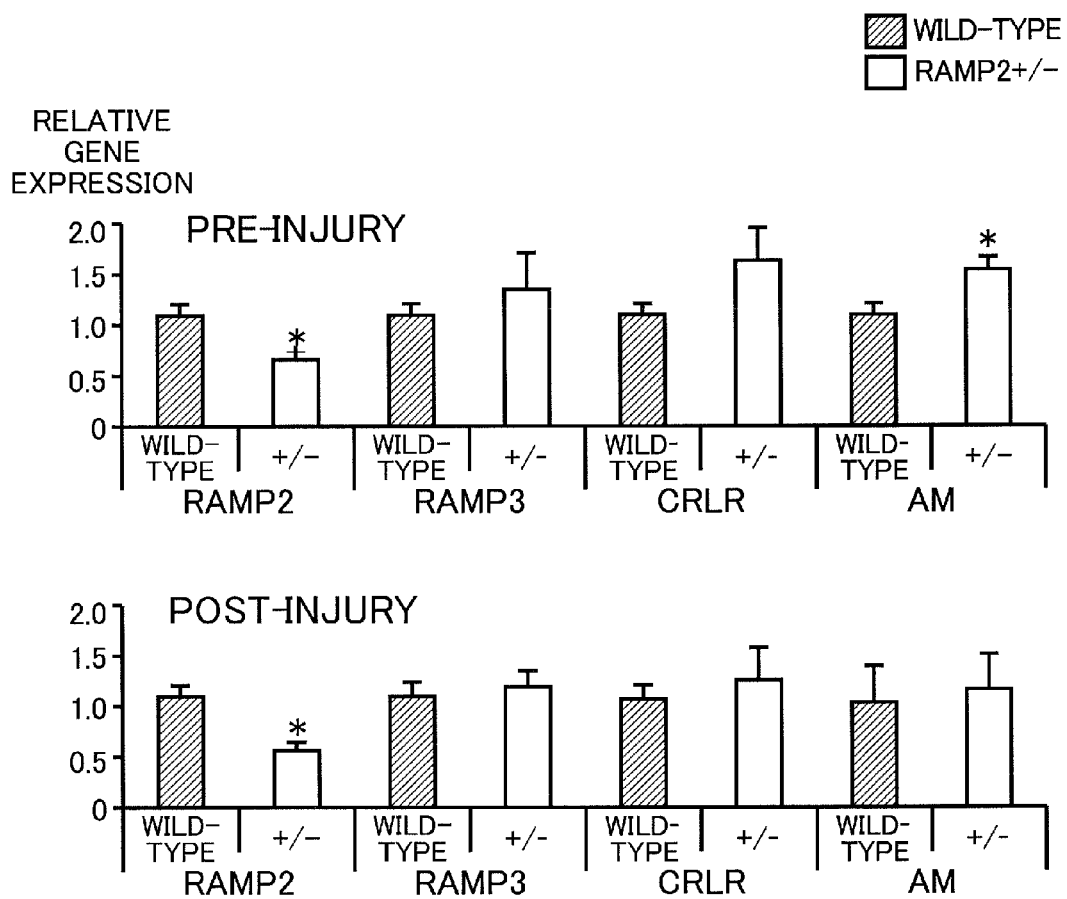
FIG. 4 is a graph showing the expression level of each gene in the femoral artery of a RAMP2+/− mouse.

As shown in FIG. 4, in a RAMP2+/− mouse, compared to a wild type mouse, the expression of RAMP2 both before and after indwelling is significantly low, while on the other hand the expression of RAMP3 and CRLR were statistically the same. This shows that the result shown by Experiment 3, i.e., the result that arteriosclerosis is further worsened in a RAMP2+/− mouse than in a wild type mouse, is due to the lower expression of RAMP2.

Further, in the state before the injury, the expression of AM is elevated in a RAMP2+/− mouse. This suggests that, even in an adult, if the expression of RAMP2 is reduced, the expression of AM is increased by positive feedback. In other words, RAMP2 plays a central role in the AM-signaling not only in the blood vessels during embryonic period, but also in the blood vessels of adult.

It can be considered that the reason why the significant difference between the AM expression in the wild type mouse and the RAMP2+/− mouse vanishes after the injury is because upregulation of AM also occurs in a wild type mouse after the injury. In a RAMP2+/− mouse, regardless of the enhanced expression of AM in the baseline (or, after the injury, regardless of the significant difference of the AM expression vanishes), the severity of arteriosclerosis is enhanced compared with a wild type mouse. It can be considered that the severe arteriosclerosis in a RAMP2+/− mouse is because the expression of RAMP2 is low even if the AM expression is upregulated and antiarteriosclerotic function of AM cannot fully work. This shows that the antiarteriosclerotic function is not sufficiently exerted only by the upregulation of AM, but upregulation of RAMP2 is necessary.

Experiment 4

Blood Vessel Occlusion

Morphology

Figure 5:
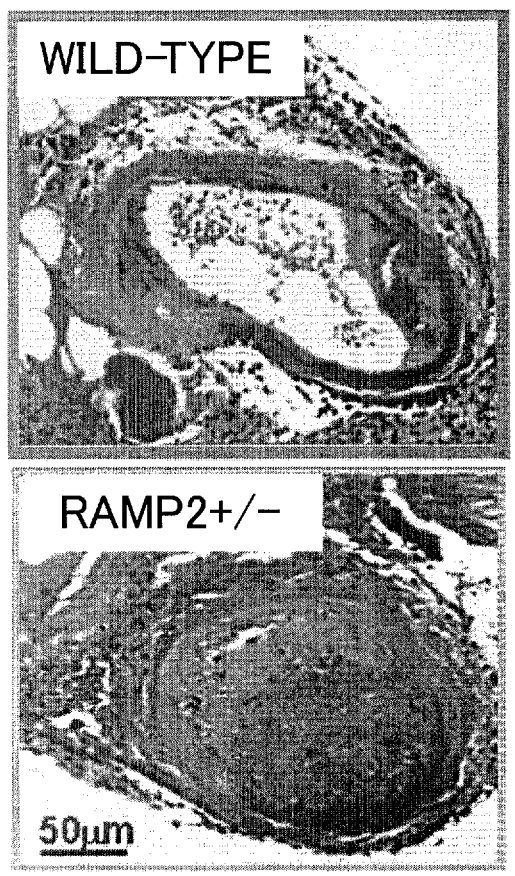
FIG. 5 is a different femoral sectional photograph of a RAMP2+/− mouse.

The outer circumference of the femoral artery of the RAMP2 hetero knockout mouse (RAMP2+/−) obtained in Experiment 1, and of a wild type mouse (RAMP2+/+) were coated with a 10% iron chloride solution, and a femur portion of each mouse was harvested 24 hours after the coating. Photographs of HE stained, slices thereof are shown in FIG. 5. Further, a cross section of the thrombus was quantified at transverse slices (n=5) of the harvested femoral arteries. Furthermore, the constriction ratio of the blood vessel was calculated based on the ratio of the cross sectional area of the thrombus and the whole area of the blood vessel lumen. The size of the thrombus and the constriction ratio of the blood vessel are respectively shown in FIG. 6 and FIG. 7.

Figure 6:
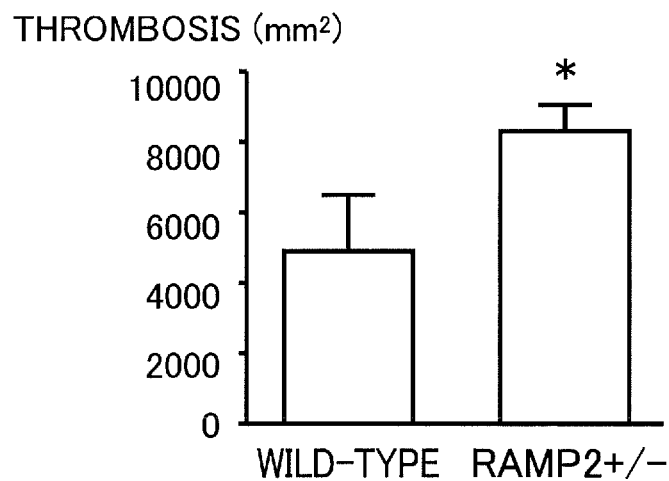
FIG. 6 is a graph showing the amount of thrombi in the femoral artery of a RAMP2+/− mouse.
Figure 7:
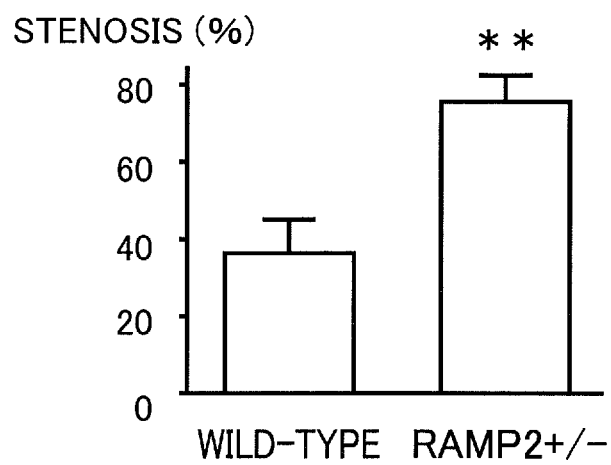
FIG. 7 is a graph showing the amount of vasoconstriction in the femoral artery of a RAMP2+/− mouse.

As shown in FIG. 5, compared to a wild type mouse, in the RAMP2+/− mouse the presence of a large thrombus was observed. This result agrees with the significantly high constriction ratio (FIG. 7) of the blood vessel and the size of the thrombus (FIG. 6). From these results, it is suggested that a reduction in the expression of RAMP2 worsens thrombosis, from the morphological viewpoint of accelerating the blood vessel blockage.

Immunology

The expression of the MCP-1 and Mac-1 proteins in the femoral artery in Experiment 4 was studied. Specifically, the femoral artery was immunostained according to the usual methods, using antibodies binding to each protein, and the results are shown in FIG. 8.

Figure 8:
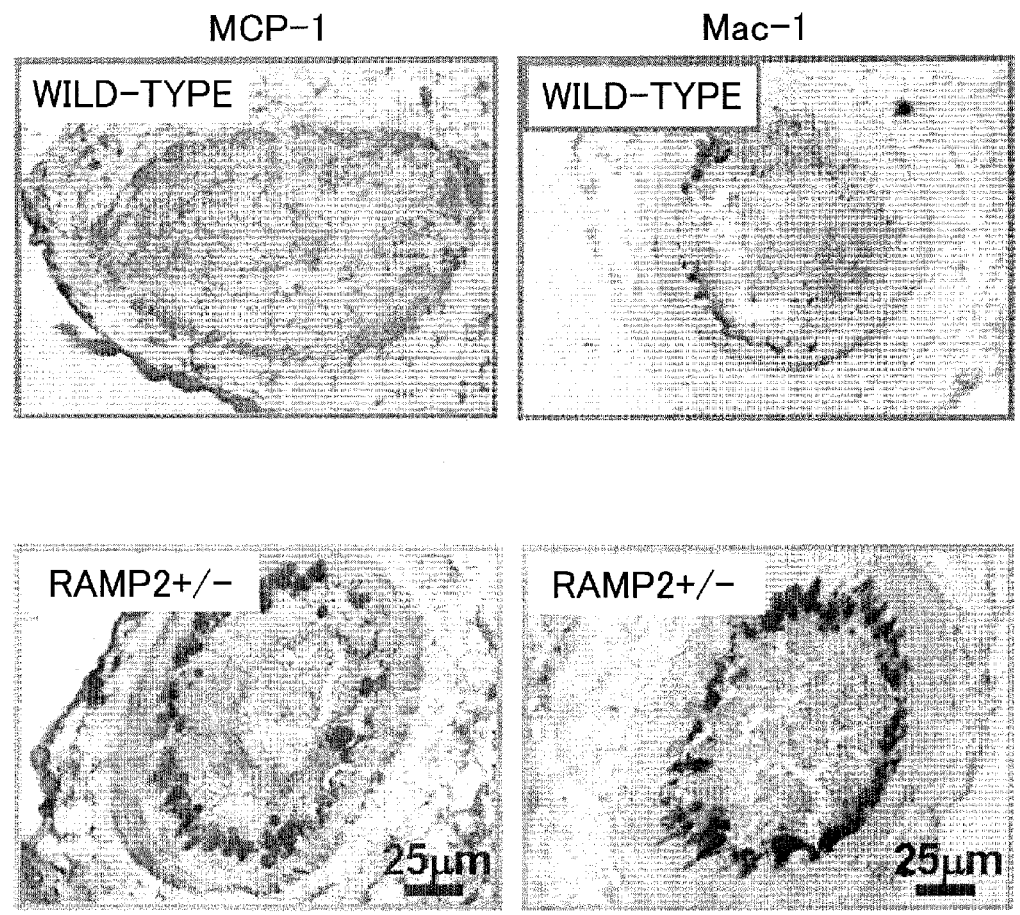
FIG. 8 is another femoral sectional photograph of a RAMP2+/− mouse.

As shown in FIG. 8, in the RAMP2+/− mouse, the MCP-1 and Mac-1 proteins were expressed across a wider range than in the wild type mouse. The MCP-1 and Mac-1 proteins are a chemokine and an adhesion molecule, which show enhanced expression with tissue inflammation, and thus, it is suggested that a stronger inflammation arises at occluded locations in a RAMP2+/− mouse than in a wild type mouse.

Experiment 5

Conditional Gene Targeting

In order to clarify the pathophysiological significance of the AM-RAMP2 system, a homozygote of a RAMP2 knockout mouse is required, but a homozygote (RAMP2−/−) is embryonic lethal. Thus, conditional gene targeting of the RAMP2 gene was carried out using a Cre-loxP system, and RAMP2 was specifically deleted from each cell type.

Vascular Endothelial Cells

Figure 9:
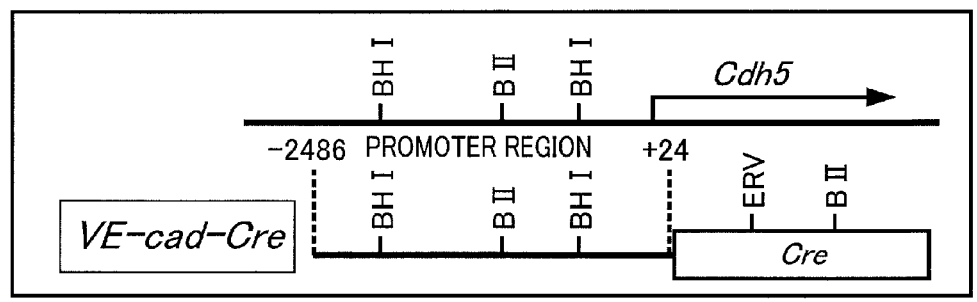
FIG. 9 is an outline diagram of a vector for endothelial cell specific knockout of the RAMP2 gene.

A flox mouse wherein the RAMP2 gene locus is held between loxP sequences was created according to the usual methods. On the other hand, a Cre mouse was created wherein a promoter sequence of VE-cadherin (Cdh5), which is specifically expressed in vascular endothelial cells, was introduced into a vector (refer to FIG. 9, and Circulation Research, 2006; 98: 897-904) positioned at the 5' side of the Cre sequence. By cross breeding the flox mouse and the Cre mouse, a mouse where the RAMP2 was knocked out specifically in vascular endothelial cells was obtained.

Figure 10:
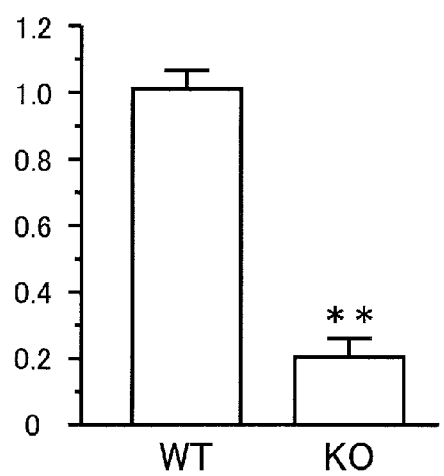
FIG. 10 is a graph showing the expression level of the RAMP2 gene in cells derived from a vascular endothelial cell-specific RAMP2 knockout mouse.

Manufactured 8 to 10 week-old adult mice were subjected to abdominal section after anesthesia, and the inside of the liver was perfused with a culture fluid containing collagenase, and isolated sinusoid endothelial cells were cultured. The total RNA extracted from these cells was reverse transcribed to cDNA, and quantitative real time PCR was carried out using a primer having a sequence specific to RAMP2. As a result, as shown in FIG. 10, it was confirmed that in a blood vessel specific RAMP2 knockout mouse, compared to a wild type mouse, RAMP2 is expressed in far smaller amounts (about 20%).

Figure 11A:
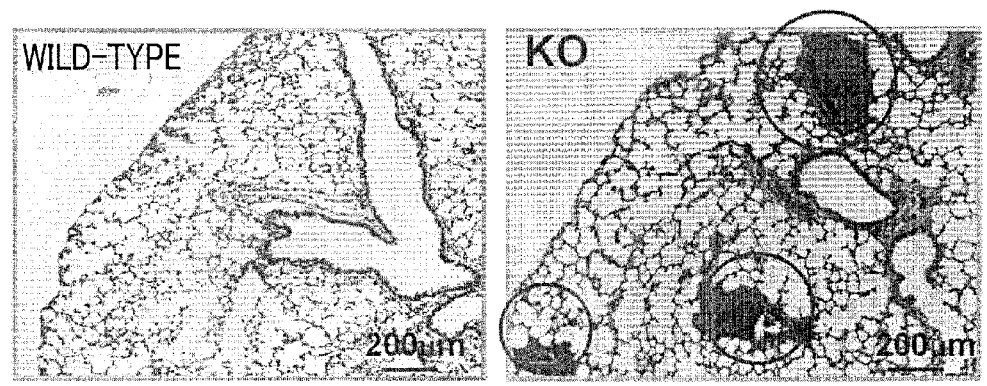
FIG. 11(a) is a photograph of a lung section harvested from a vascular endothelial cell-specific RAMP2 knockout mouse, and 11(b) is an enlargement of a portion thereof.
Figure 11B:
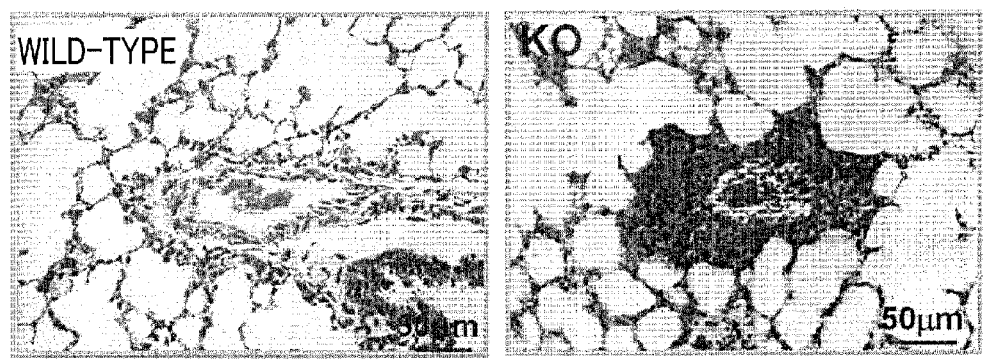

Further, the lungs were harvested from a blood vessel specific RAMP2 knockout mouse and a wild type mouse, and photographs of HE stained slices of the lungs are shown in FIG. 11. As shown in FIG. 11(a) and FIG. 11(b) (an enlargement of a portion of FIG. 11(a)), occurrence of severe inflammation was observed in knockout mouse (the portions surrounded by circles).

Figure 12A:
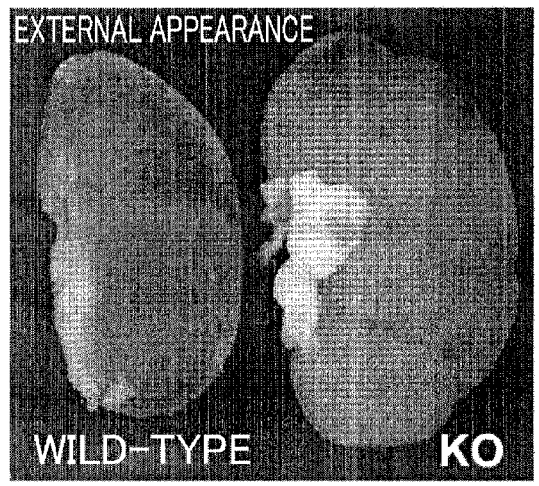
FIG. 12(a) is an photograph of the external appearance, 12(b) a cross sectional photograph, and 12(c) a section photograph of the kidney harvested from a vascular endothelial cell-specific RAMP2 knockout mouse.
Figure 12B:
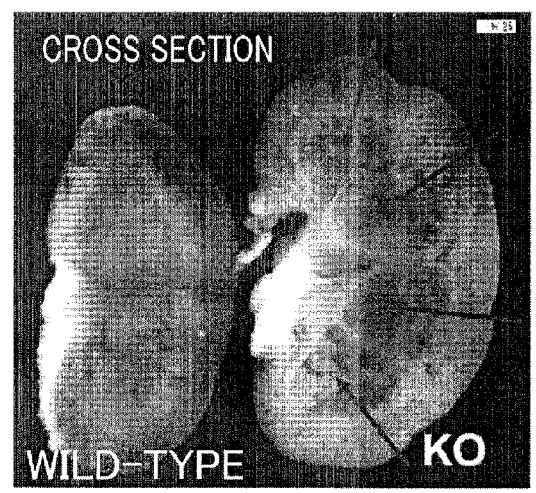
Figure 12C:
Figure 13:
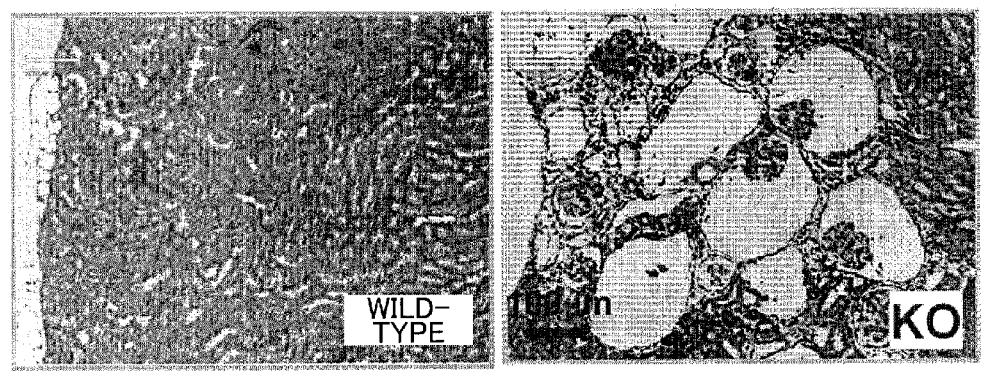
FIG. 13 is an enlargement of a portion of FIG. 12(c).

Next, kidneys were harvested from a blood vessel specific RAMP2 knockout mouse and a wild type mouse, and photographs of the external appearance of these kidneys are shown in FIG. 12(a), cross sectional photographs are shown in FIG. 12(b), and photographs of HE stained slices are shown in FIG. 12(c), and enlargements of portions of FIG. 12(c) are respectively shown in FIG. 13. In the knockout mouse, compared to the wild type mouse, kidney disorders such as overall swelling (refer to FIG. 12(a)), glomerulosclerosis, cyst formation, and hydronephrosis were observed (refer to FIGS. 12(b) and (c), and FIG. 13).

Based on the results of FIG. 10 to FIG. 13, it is suggested that a reduction in the expression of RAMP2 can facilitate lesions in various organs.

Cardiac Myocytes

Figure 14:
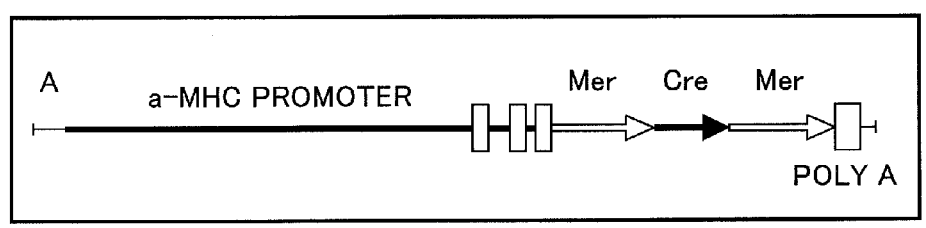
FIG. 14 is a outline diagram of a different vector for cardiac myocyte-specific knockout of the RAMP2 gene.

A Cre mouse was created by introducing a vector wherein a promoter sequence of α-MHC, which is expressed specifically in cardiac myocytes, was positioned at the 5' side of the Cre sequence, and further, a mutant estrogen receptor (Mer) to which tamoxifen binds was positioned at both sides of the Cre (refer to FIG. 14, Circ. Res. 2001, 89; 20-25). Except for the point of using this Cre mouse, using the same procedure as above, cardiac myocyte-specific RAMP2 knockout mice were obtained.

Figure 15A:
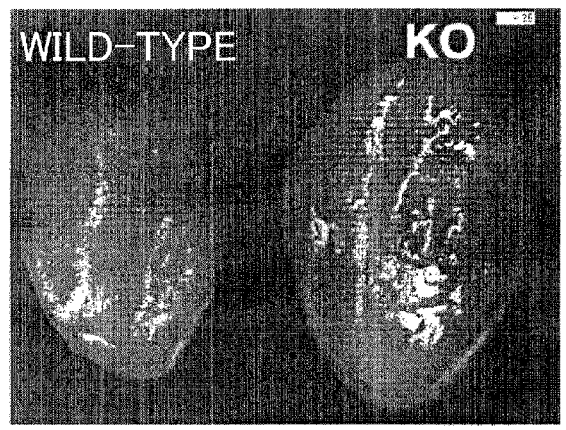
FIG. 15(a) is a photograph of the external appearance, and 15(b) a photograph of the section of heart harvested from a cardiac myocyte-specific RAMP2 knockout mouse.
Figure 15B:
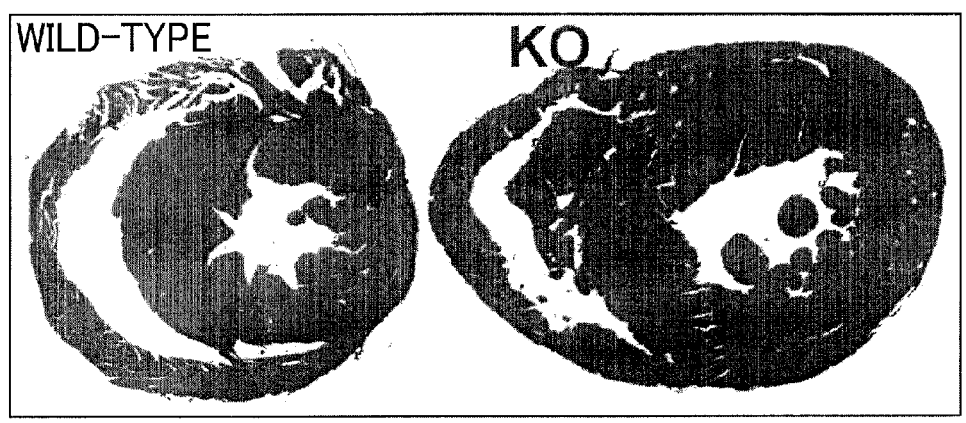
Figure 17:
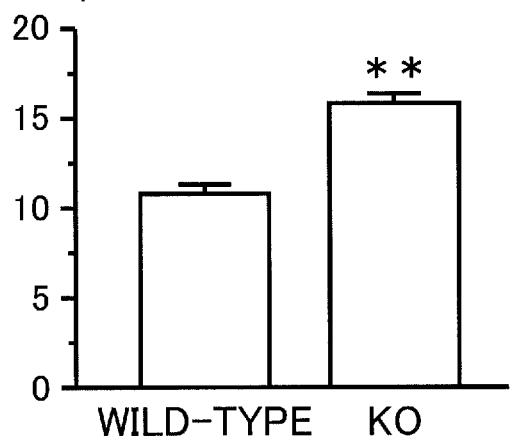
FIG. 17 is a graph showing the transverse diameters of the cardiac myocytes of the heart of FIG. 15.

The manufactured mice were given an intraabdominal administration of 30 mg/kg/day of tamoxifen, and one week after the start of the administration, the hearts were harvested. FIG. 15(a) shows a photograph of the external appearance of these hearts, and FIG. 15(b) shows a photograph of Masson's trichrome stained slice. Further, FIG. 17 shows the results of measuring the transverse diameter of the cardiac myocytes in a cross sectional tissue slice of the hearts. As shown by FIGS. 15(a) and 15(b), in the cardiac myocyte-specific RAMP2 knockout mice, compared to the wild type mice, it was confirmed that the heart is enlarged, and this heart enlargement accompanies the enlargement of the cardiac myocytes (FIG. 17). These symptoms are conjectured to be caused by a reduction in the RAMP2 expression.

Figure 16:
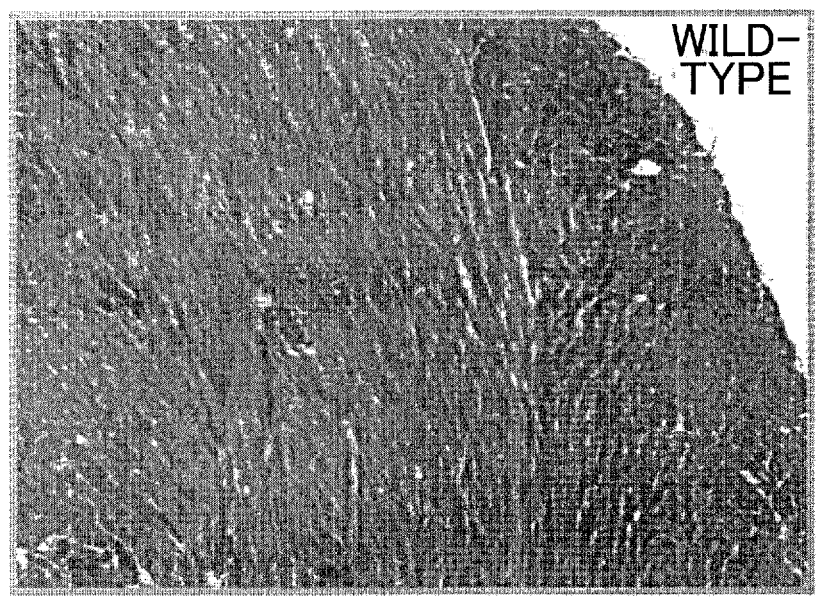
FIG. 16 is an enlargement of a portion of FIG. 15(b).
Figure 16:
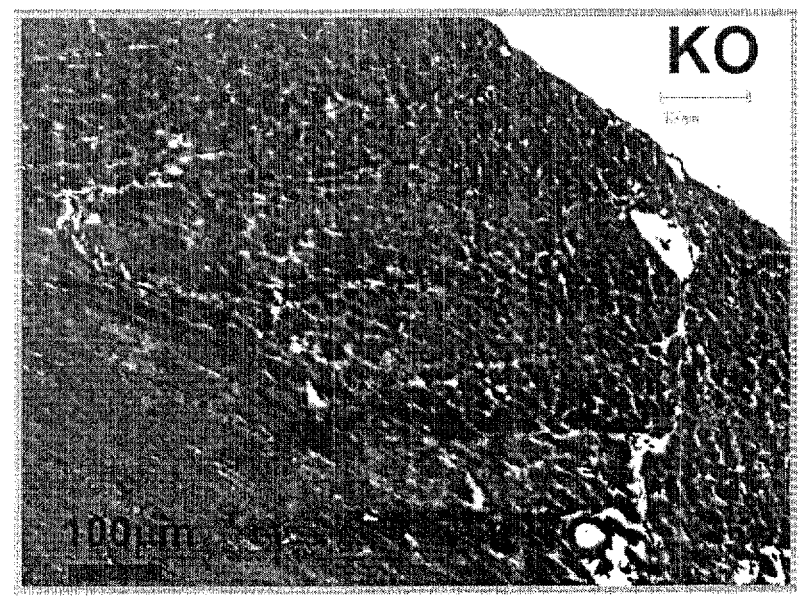

An enlargement of a portion of FIG. 15(b) is shown in FIG. 16. As shown in FIG. 16, in the cardiac myocyte-specific RAMP2 knockout mice, many fibrotic lesions were observed, on the other hand, such lesions were not observed in the wild type mice. This fibrosis of the heart can be conjectured to be caused by a reduction in the expression of RAMP2.

INDUSTRIAL APPLICABILITY

From the above results, it is indicated that various physiological actions of AM are regulated by RAMP2, in other words, by targeting RAMP2, it is possible to artificially manipulate the physiological functions of AM, and it is possible to comprehensively treat or prevent metabolic syndrome. Because RAMP2 is a low molecular, one-transmembrane protein, it not only has a long half life in blood and excellent in vivo stability, but also its structural analysis and the search for low molecular compound which can artificially control this system, and the like, are easy. Because of this, RAMP2 is very promising as a therapeutic target molecule.

SEQUENCE LISTING

NSTF-001 Sequence Listing.txt

The invention claimed is:

1. A screening method for a therapeutic drug for metabolic syndrome, comprising:
    a step of bringing into contact a test substance and a polypeptide having the amino acid sequence identified as SEQ ID NO:2, and which binds to calcitonin receptor-like receptor (CRLR); and
    a step of detecting binding between the polypeptide and the test substance.

* * * * *

SEQUENCE LISTING

```
<160> NUMBER OF SEQ ID NOS: 6

<210> SEQ ID NO 1
<211> LENGTH: 501
<212> TYPE: DNA
<213> ORGANISM: Homo sapiens

<400> SEQUENCE: 1
atggcctcgc tccgggtgga gcgcgccggc ggcccgcgtc tccctaggac ccgagtcggg      60
cggccggcag ccgtccgcct cctccttctg ctgggcgctg tcctgaatcc ccacgaggcc     120
ctggctcagc ctcttccccac acaggcaca ccagggtcag aagggggac ggtgaagaac      180 tatgagacag ctgtccaatt ttgctggaat cattataagg atcaaatgga tcctatcgaa     240
aaggattggt gcgactgggc catgattagc aggccttata gcaccctgcg agattgcctg     300
gagcactttg cagagttgtt tgacctgggc ttccccaatc ccttggcaga gaggatcatc     360
tttgagactc accagatcca ctttgccaac tgctccctgg tgcagcccac cttctctgac     420
cccccagagg atgtactcct ggccatgatc atagccccca tctgcctcat ccccttcctc     480
atcactcttg tagtatggag g                                               501

<210> SEQ ID NO 2
<211> LENGTH: 167
<212> TYPE: PRT
<213> ORGANISM: Homo sapiens

<400> SEQUENCE: 2

Met Ala Ser Leu Arg Val Glu Arg Ala Gly Gly Pro Arg Leu Pro Arg
1               5                   10                  15

Thr Arg Val Gly Arg Pro Ala Ala Val Arg Leu Leu Leu Leu Leu Gly
                20                  25                  30

Ala Val Leu Asn Pro His Glu Ala Leu Ala Gln Pro Leu Pro Thr Thr
            35                  40                  45

Gly Thr Pro Gly Ser Glu Gly Gly Thr Val Lys Asn Tyr Glu Thr Ala
        50                  55                  60

Val Gln Phe Cys Trp Asn His Tyr Lys Asp Gln Met Asp Pro Ile Glu
65                  70                  75                  80

Lys Asp Trp Cys Asp Trp Ala Met Ile Ser Arg Pro Tyr Ser Thr Leu
                85                  90                  95

Arg Asp Cys Leu Glu His Phe Ala Glu Leu Phe Asp Leu Gly Phe Pro
            100                 105                 110

Asn Pro Leu Ala Glu Arg Ile Ile Phe Glu Thr His Gln Ile His Phe
        115                 120                 125

Ala Asn Cys Ser Leu Val Gln Pro Thr Phe Ser Asp Pro Pro Glu Asp
    130                 135                 140

Val Leu Leu Ala Met Ile Ile Ala Pro Ile Cys Leu Ile Pro Phe Leu
145                 150                 155                 160
```

```
Ile Thr Leu Val Val Trp Arg
              165

<210> SEQ ID NO 3
<211> LENGTH: 780
<212> TYPE: DNA
<213> ORGANISM: Homo sapiens
<220> FEATURE:
<221> NAME/KEY: CDS
<222> LOCATION: (69)..(596)

<400> SEQUENCE: 3
ggatataggc gcccccacac ccgggcccgg ctaagcgccg ccgccgctcc tcgcctcctt      60 gctgcacg atg gcc tcg ctc cgg gtg gag cgc gcc ggc ggc ccg cgt ctc     110
         Met Ala Ser Leu Arg Val Glu Arg Ala Gly Gly Pro Arg Leu
           1               5                  10 cct agg acc cga gtc ggg cgg ccg gca gcc gtc cgc ctc ctc ctt ctg     158
Pro Arg Thr Arg Val Gly Arg Pro Ala Ala Val Arg Leu Leu Leu Leu
 15              20                  25                  30 ctg ggc gct gtc ctg aat ccc cac gag gcc ctg gct cag cct ctt ccc     206
Leu Gly Ala Val Leu Asn Pro His Glu Ala Leu Ala Gln Pro Leu Pro
             35                  40                  45 acc aca ggc aca cca ggg tca gaa ggg ggg acg gtg aag aac tat gag     254
Thr Thr Gly Thr Pro Gly Ser Glu Gly Gly Thr Val Lys Asn Tyr Glu
         50                  55                  60 aca gct gtc caa ttt tgc tgg aat cat tat aag gat caa atg gat cct     302
Thr Ala Val Gln Phe Cys Trp Asn His Tyr Lys Asp Gln Met Asp Pro
     65                  70                  75 atc gaa aag gat tgg tgc gac tgg gcc atg att agc agg cct tat agc     350
Ile Glu Lys Asp Trp Cys Asp Trp Ala Met Ile Ser Arg Pro Tyr Ser
 80                  85                  90 acc ctg cga gat tgc ctg gag cac ttt gca gag ttg ttt gac ctg ggc     398
Thr Leu Arg Asp Cys Leu Glu His Phe Ala Glu Leu Phe Asp Leu Gly
 95                 100                 105                 110 ttc ccc aat ccc ttg gca gag agg atc atc ttt gag act cac cag atc     446
Phe Pro Asn Pro Leu Ala Glu Arg Ile Ile Phe Glu Thr His Gln Ile
             115                 120                 125 cac ttt gcc aac tgc tcc ctg gtg cag ccc acc ttc tct gac ccc cca     494
His Phe Ala Asn Cys Ser Leu Val Gln Pro Thr Phe Ser Asp Pro Pro
         130                 135                 140 gag gat gta ctc ctg gcc atg atc ata gcc ccc atc tgc ctc atc ccc     542
Glu Asp Val Leu Leu Ala Met Ile Ile Ala Pro Ile Cys Leu Ile Pro
     145                 150                 155 ttc ctc atc act ctt gta gta tgg agg agt aaa gac agt gag gcc cag     590
Phe Leu Ile Thr Leu Val Val Trp Arg Ser Lys Asp Ser Glu Ala Gln
 160                 165                 170 gcc tag ggggcacgag cttctcaaca accatgttac tccacttccc caccccacc       646
Ala
175 aggcctccct cctcccctcc tactcccttt tctcactctc atccccacca cagatccctg    706 gattgctggg aatggaagcc agggttgggc atggcacaag ttctgtaatc ttcaaaataa    766 aactttttt ttga                                                      780

<210> SEQ ID NO 4
<211> LENGTH: 2984
<212> TYPE: DNA
<213> ORGANISM: Homo sapiens
<220> FEATURE:
<221> NAME/KEY: CDS
<222> LOCATION: (506)..(1891)
```

<400> SEQUENCE: 4

```
gaacaacctc tctctctcca gcagagagtg tcacctcctg ctttaggacc atcaagctct      60
gctaactgaa tctcatccta attgcaggat cacattgcaa agctttcact ctttcccacc     120
ttgcttgtgg gtaaatctct tctgcggaat ctcagaaagt aaagttccat cctgagaata     180
tttcacaaag aatttcctta agagctggac tgggtcttga cccctgaatt taagaaattc     240
ttaaagacaa tgtcaaatat gatccaagag aaaatgtgat ttgagtctgg agacaattgt     300
gcatatcgtc taataataaa aacccatact agcctataga aaacaatatt tgaaagattg     360
ctaccactaa aagaaaact actacaactt gacaagactg ctgcaaactt caatttgtca      420
accacaactt gacaaggttg ctataaaaca agattgctac aacttctagt ttatgttata     480
cagcatattt cattttggct taatg atg gag aaa aag tgt acc ctg tat ttt       532
                            Met Glu Lys Lys Cys Thr Leu Tyr Phe
                             1               5 ctg gtt ctc ttg cct ttt ttt atg att ctt gtt aca gca gaa tta gaa       580
Leu Val Leu Leu Pro Phe Phe Met Ile Leu Val Thr Ala Glu Leu Glu
 10              15                  20                  25 gag agt cct gag gac tca att cag ttg gga gtt act aga aat aaa atc       628
Glu Ser Pro Glu Asp Ser Ile Gln Leu Gly Val Thr Arg Asn Lys Ile
             30                  35                  40 atg aca gct caa tat gaa tgt tac caa aag att atg caa gac ccc att       676
Met Thr Ala Gln Tyr Glu Cys Tyr Gln Lys Ile Met Gln Asp Pro Ile
         45                  50                  55 caa caa gca gaa ggc gtt tac tgc aac aga acc tgg gat gga tgg ctc       724
Gln Gln Ala Glu Gly Val Tyr Cys Asn Arg Thr Trp Asp Gly Trp Leu
     60                  65                  70 tgc tgg aac gat gtt gca gca gga act gaa tca atg cag ctc tgc cct       772
Cys Trp Asn Asp Val Ala Ala Gly Thr Glu Ser Met Gln Leu Cys Pro
 75                  80                  85 gat tac ttt cag gac ttt gat cca tca gaa aaa gtt aca aag atc tgt       820
Asp Tyr Phe Gln Asp Phe Asp Pro Ser Glu Lys Val Thr Lys Ile Cys
 90                  95                 100                 105 gac caa gat gga aac tgg ttt aga cat cca gca agc aac aga aca tgg       868
Asp Gln Asp Gly Asn Trp Phe Arg His Pro Ala Ser Asn Arg Thr Trp
                110                 115                 120 aca aat tat acc cag tgt aat gtt aac acc cac gag aaa gtg aag act       916
Thr Asn Tyr Thr Gln Cys Asn Val Asn Thr His Glu Lys Val Lys Thr
            125                 130                 135 gca cta aat ttg ttt tac ctg acc ata att gga cac gga ttg tct att       964
Ala Leu Asn Leu Phe Tyr Leu Thr Ile Ile Gly His Gly Leu Ser Ile
        140                 145                 150 gca tca ctg ctt atc tcg ctt gga ata ttc ttt tat ttc aag agc cta      1012
Ala Ser Leu Leu Ile Ser Leu Gly Ile Phe Phe Tyr Phe Lys Ser Leu
    155                 160                 165 agt tgc caa agg att acc tta cac aaa aat ctg ttc ttc tca ttt gtt      1060
Ser Cys Gln Arg Ile Thr Leu His Lys Asn Leu Phe Phe Ser Phe Val
170                 175                 180                 185 tgt aac tct gtt gta aca atc att cac ctc act gca gtg gcc aac aac      1108
Cys Asn Ser Val Val Thr Ile Ile His Leu Thr Ala Val Ala Asn Asn
                190                 195                 200 cag gcc tta gta gcc aca aat cct gtt agt tgc aaa gtg tcc cag ttc      1156
Gln Ala Leu Val Ala Thr Asn Pro Val Ser Cys Lys Val Ser Gln Phe
            205                 210                 215 att cat ctt tac ctg atg ggc tgt aat tac ttt tgg atg ctc tgt gaa      1204
Ile His Leu Tyr Leu Met Gly Cys Asn Tyr Phe Trp Met Leu Cys Glu
        220                 225                 230 ggc att tac cta cac aca ctc att gtg gtg gcc gtg ttt gca gag aag      1252
```

```
Gly Ile Tyr Leu His Thr Leu Ile Val Val Ala Val Phe Ala Glu Lys
    235             240                 245 caa cat tta atg tgg tat tat ttt ctt ggc tgg gga ttt cca ctg att    1300
Gln His Leu Met Trp Tyr Tyr Phe Leu Gly Trp Gly Phe Pro Leu Ile
250             255                 260                 265 cct gct tgt ata cat gcc att gct aga agc tta tat tac aat gac aat    1348
Pro Ala Cys Ile His Ala Ile Ala Arg Ser Leu Tyr Tyr Asn Asp Asn
                270                 275                 280 tgc tgg atc agt tct gat acc cat ctc ctc tac att atc cat ggc cca    1396
Cys Trp Ile Ser Ser Asp Thr His Leu Leu Tyr Ile Ile His Gly Pro
                285                 290                 295 att tgt gct gct tta ctg gtg aat ctt ttt ttc ttg tta aat att gta    1444
Ile Cys Ala Ala Leu Leu Val Asn Leu Phe Phe Leu Leu Asn Ile Val
            300                 305                 310 cgc gtt ctc atc acc aag tta aaa gtt aca cac caa gcg gaa tcc aat    1492
Arg Val Leu Ile Thr Lys Leu Lys Val Thr His Gln Ala Glu Ser Asn
        315                 320                 325 ctg tac atg aaa gct gtg aga gct act ctt atc ttg gtg cca ttg ctt    1540
Leu Tyr Met Lys Ala Val Arg Ala Thr Leu Ile Leu Val Pro Leu Leu
330                 335                 340                 345 ggc att gaa ttt gtg ctg att cca tgg cga cct gaa gga aag att gca    1588
Gly Ile Glu Phe Val Leu Ile Pro Trp Arg Pro Glu Gly Lys Ile Ala
                350                 355                 360 gag gag gta tat gac tac atc atg cac atc ctt atg cac ttc cag ggt    1636
Glu Glu Val Tyr Asp Tyr Ile Met His Ile Leu Met His Phe Gln Gly
                365                 370                 375 ctt ttg gtc tct acc att ttc tgc ttc ttt aat gga gag gtt caa gca    1684
Leu Leu Val Ser Thr Ile Phe Cys Phe Phe Asn Gly Glu Val Gln Ala
            380                 385                 390 att ctg aga aga aac tgg aat caa tac aaa atc caa ttt gga aac agc    1732
Ile Leu Arg Arg Asn Trp Asn Gln Tyr Lys Ile Gln Phe Gly Asn Ser
        395                 400                 405 ttt tcc aac tca gaa gct ctt cgt agt gcg tct tac aca gtg tca aca    1780
Phe Ser Asn Ser Glu Ala Leu Arg Ser Ala Ser Tyr Thr Val Ser Thr
410                 415                 420                 425 atc agt gat ggt cca ggt tat agt cat gac tgt cct agt gaa cac tta    1828
Ile Ser Asp Gly Pro Gly Tyr Ser His Asp Cys Pro Ser Glu His Leu
                430                 435                 440 aat gga aaa agc atc cat gat att gaa aat gtt ctc tta aaa cca gaa    1876
Asn Gly Lys Ser Ile His Asp Ile Glu Asn Val Leu Leu Lys Pro Glu
                445                 450                 455 aat tta tat aat tga aaatagaagg atggttgtct cactgttttg tgcttctcct    1931
Asn Leu Tyr Asn
        460 aactcaagga cttggaccca tgactctgta gccagaagac ttcaatatta aatgactttt    1991 tgaatgtcat aaagaagagc cttcacatga aattagtagt gtgttgataa gagtgtaaca    2051 tccagctcta tgtgggaaaa aagaaatcct ggtttgtaat gtttgtcagt aaatactccc    2111 actatgcctg atgtgacgct actaacctga catcaccaag tgtggaattg agaaaagca     2171 caatcaactt ttctgagctg gtgtaagcca gttccagcac accattgcat gaattcacaa    2231 acaaatggct gtaaaactaa acatacatgt tgggcatgat tctacccttc ttgccccaag    2291 agacctagct aaggtctata aacatgaagg gaaaattagc ttttagtttt aaaactcttt    2351 atcccatctt gattggggca gttgactttt tttttgccca gagtgccgta gtcctttttg    2411 taactcccct ctcaaatgga caataccaga agtgaattat ccctgctggc tttcttttct    2471 ctatgaaaag caactgagta caattgttat gatctactca tttgctgaca catcagttat    2531
```

```
atcttgtggc atatccattg tggaaactgg atgaacagga tgtataatat gcaatcctac    2591
ttctatatca ttaggaaaac atcttagttg atgctacaaa acaccttgtc aacctcttcc    2651
tgtcttacca aacagtggga gggaattcct agctgtaaat ataaattttg tcccttccat    2711
ttctactgta taaacaaatt agcaatcatt ttatataaag aaaatcaatg aaggatttct    2771
tattttcttg gaattttgta aaagaaatt gtgaaaaatg agcttgtaaa tactccatta     2831
ttttatttta tagtctcaaa tcaaatacat acaacctatg taatttttaa agcaaatata    2891
taatgcaaca atgtgtgtat gttaatatct gatactgtat ctgggctgat tttttaaata   2951
aaatagagtc tggaatgcta aaaaaaaaaa aaa                                 2984
```

```
<210> SEQ ID NO 5
<211> LENGTH: 1449
<212> TYPE: DNA
<213> ORGANISM: Homo sapiens
<220> FEATURE:
<221> NAME/KEY: CDS
<222> LOCATION: (439)..(594)

<400> SEQUENCE: 5
```

```
ctggatagaa cagctcaagc cttgccactt cgggcttctc actgcagctg ggcttggact      60
tcggagtttt gccattgcca gtgggacgtc tgagactttc tccttcaagt acttggcaga    120
tcactctctt agcagggtct cgcttcgca gccgggatga agctggtttc cgtcgccctg     180
atgtacctgg gttcgctcgc cttcctaggc gctgacaccg ctcggttgga tgtcgcgtcg    240
gagtttcgaa agaagtggaa taagtgggct ctgagtcgtg ggaagaggga actgcggatg    300
tccagcagct accccaccgg gctcgctgac gtgaaggccg ggcctgccca gacccttatt    360
cggccccagg acatgaaggg tgcctctcga agccccgaag acagcagtcc ggatgccgcc    420
cgcatccgag tcaagcgc tac cgc cag agc atg aac aac ttc cag ggc ctc      471
                    Tyr Arg Gln Ser Met Asn Asn Phe Gln Gly Leu
                     1               5                  10 cgg agc ttt ggc tgc cgc ttc ggg acg tgc acg gtg cag aag ctg gca      519
Arg Ser Phe Gly Cys Arg Phe Gly Thr Cys Thr Val Gln Lys Leu Ala
         15                  20                  25 cac cag atc tac cag ttc aca gat aag gac aag gac aac gtc gcc ccc      567
His Gln Ile Tyr Gln Phe Thr Asp Lys Asp Lys Asp Asn Val Ala Pro
     30                  35                  40 agg agc aag atc agc ccc cag ggc tac ggccgccggc gccggcgctc             614
Arg Ser Lys Ile Ser Pro Gln Gly Tyr
 45                  50 cctgcccgag gccggcccgg gtcggactct ggtgtcttct aagccacaag cacacggggc    674
tccagccccc ccgagtggaa gtgctcccca ctttctttag gatttaggcg cccatggtac    734
aaggaatagt cgcgcaagca tcccgctggt gcctcccggg acgaaggact tcccgagcgg    794
tgtggggacc gggctctgac agccctgcgg agaccctgag tccgggaggc accgtccggc    854
ggcgagctct ggctttgcaa gggcccctcc ttctgggggc ttcgcttcct tagccttgct    914
caggtgcaag tgcccagggg gcggggtgc agaagaatcc gagtgtttgc caggcttaag     974
gagaggagaa actgagaaat gaatgctgag accccggag cagggtctg agccacagcc      1034 gtgctcgccc acaaactgat ttctcacggc gtgtcacccc accagggcgc aagcctcact    1094
attacttgaa ctttccaaaa cctaaagagg aaaagtgcaa tgcgtgttgt acatacagag    1154
gtaactatca atatttaagt tgttgctgt caagatttt tttgtaactt caaatataga      1214 gatattttg tacgttatat attgtattaa gggcatttta aaagcaatta tattgtcctc    1274
```

-continued

```
ccctatttta agacgtgaat gtctcagcga ggtgtaaagt tgttcgccgc gtggaatgtg    1334
agtgtgtttg tgtgcatgaa agagaaagac tgattacctc ctgtgtggaa gaaggaaaca    1394
ccgagtctct gtataatcta tttacataaa atgggtgata tgcgaacagc aaacc         1449
```

<210> SEQ ID NO 6
<211> LENGTH: 52
<212> TYPE: PRT
<213> ORGANISM: Homo sapiens

<400> SEQUENCE: 6

```
Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
                20                  25                  30

Phe Thr Asp Lys Asp Lys Asp Asn Val Ala Pro Arg Ser Lys Ile Ser
            35                  40                  45

Pro Gln Gly Tyr
        50
```